US009466131B2

(12) United States Patent
Ohishi et al.

(10) Patent No.: US 9,466,131 B2
(45) Date of Patent: Oct. 11, 2016

(54) MEDICAL IMAGE PROCESSING DEVICE

(71) Applicant: TOSHIBA MEDICAL SYSTEMS CORPORATION, Otawara-Shi, Tochigi-Ken (JP)

(72) Inventors: Satoru Ohishi, Otawara (JP); Yuko Wakayama, Osaka (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 0 days.

(21) Appl. No.: 13/858,005

(22) Filed: Apr. 6, 2013

(65) Prior Publication Data
US 2013/0223719 A1 Aug. 29, 2013

Related U.S. Application Data

(63) Continuation of application No. PCT/JP2011/073232, filed on Oct. 7, 2011.

(30) Foreign Application Priority Data

Oct. 8, 2010 (JP) ................................. 2010-228844

(51) Int. Cl.
G06T 11/00 (2006.01)
A61B 6/00 (2006.01)
(Continued)

(52) U.S. Cl.
CPC ............ *G06T 11/003* (2013.01); *A61B 6/032* (2013.01); *A61B 6/12* (2013.01); *A61B 6/466* (2013.01); *A61B 6/481* (2013.01); *A61B 6/504* (2013.01); *A61B 6/5205* (2013.01); *A61B 6/5235* (2013.01); *A61B 17/12118* (2013.01); *A61B 6/4441* (2013.01); *A61B 2090/364* (2016.02); *A61B 2090/3764* (2016.02); *A61F 2002/823* (2013.01)

(58) Field of Classification Search
None
See application file for complete search history.

(56) References Cited

U.S. PATENT DOCUMENTS 6,775,405 B1 * 8/2004 Zhu .................. G06K 9/6212
345/419
8,457,374 B2 * 6/2013 Lendl ................. G06K 9/3216
382/128

(Continued)

FOREIGN PATENT DOCUMENTS

CN 101028193 A 9/2007
JP 3-182233 A 8/1991

(Continued)

OTHER PUBLICATIONS

International Search Report for corresponding International Application No. PCT/JP2011/073232 mailed on Dec. 27, 2011.

(Continued)

*Primary Examiner* — Matthew Bella
*Assistant Examiner* — Soo Shin
(74) *Attorney, Agent, or Firm* — Ken I Yoshida

(57) ABSTRACT

A medical image processing device according to an embodiment includes a first reconstruction unit, a second reconstruction unit, and an image combining unit. The first reconstruction unit generates a first reconstructed image on the basis of an X-ray collection image using a first reconstruction filter. The second reconstruction unit generates a second reconstructed image on the basis of the X-ray collection image, using a second reconstruction filter having a high-frequency emphasis effect more than that of the first reconstruction filter. The image combining unit combines the first reconstructed image with the second reconstructed image.

9 Claims, 18 Drawing Sheets

(51) Int. Cl.
*A61B 6/03* (2006.01)
*A61B 6/12* (2006.01)
*A61B 17/12* (2006.01)
*A61F 2/82* (2013.01)

(56) References Cited

U.S. PATENT DOCUMENTS

| | | | |
|---|---|---|---|
| 2002/0048343 A1* | 4/2002 | Launay | A61B 6/481 378/98.12 |
| 2002/0087069 A1* | 7/2002 | Ho | G01R 33/56375 600/415 |
| 2004/0101088 A1* | 5/2004 | Sabol | A61B 6/504 378/4 |
| 2006/0038146 A1 | 2/2006 | Arakawa | |
| 2007/0140537 A1* | 6/2007 | Heigl | G06T 15/08 382/128 |
| 2007/0206724 A1* | 9/2007 | Sakaguchi | A61B 6/504 378/62 |
| 2008/0137935 A1* | 6/2008 | Spahn | G06T 5/50 382/132 |
| 2010/0142792 A1* | 6/2010 | Sakaguchi | A61B 6/00 382/132 |
| 2011/0037761 A1* | 2/2011 | Mistretta | A61B 6/4441 345/419 |
| 2011/0081057 A1* | 4/2011 | Zeng | G06T 7/0012 382/128 |

FOREIGN PATENT DOCUMENTS

| | | |
|---|---|---|
| JP | 08-140964 A | 6/1996 |
| JP | 9-44645 A | 2/1997 |
| JP | 2001-283215 A | 10/2001 |
| JP | 2004-313391 A | 11/2004 |
| JP | 2005-5846 A | 1/2005 |
| JP | 2005-080285 A | 3/2005 |
| JP | 2005-512372 A | 4/2005 |
| JP | 2005-296332 A | 10/2005 |
| JP | 2005-349079 A | 12/2005 |
| JP | 2006-58655 A | 3/2006 |
| JP | 2007-229254 A | 9/2007 |
| JP | 2007-534420 A | 11/2007 |
| JP | 2009-022459 A | 2/2009 |
| JP | 2009-82646 A | 4/2009 |
| JP | 2009-532162 A | 9/2009 |
| JP | 2010-131371 A | 6/2010 |

OTHER PUBLICATIONS

Chinese Office Action with its English Translation for Chinese Patent Application No. 201180003798.X mailed on Nov. 28, 2013.
Japanese Office Action with its English summary for a corresponding Japanese Patent Application No. 2011-222903 mailed on May 19, 2015.

* cited by examiner

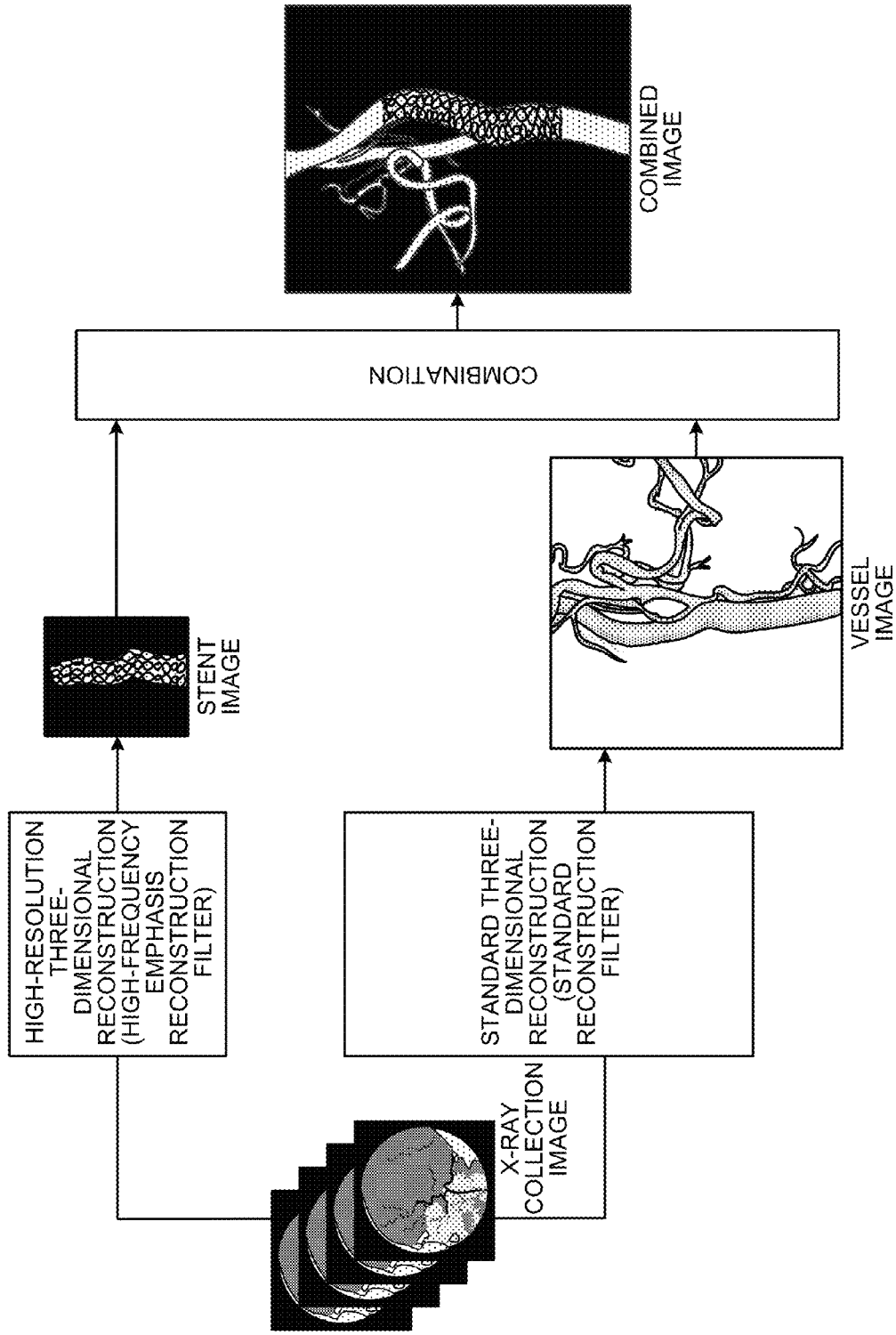

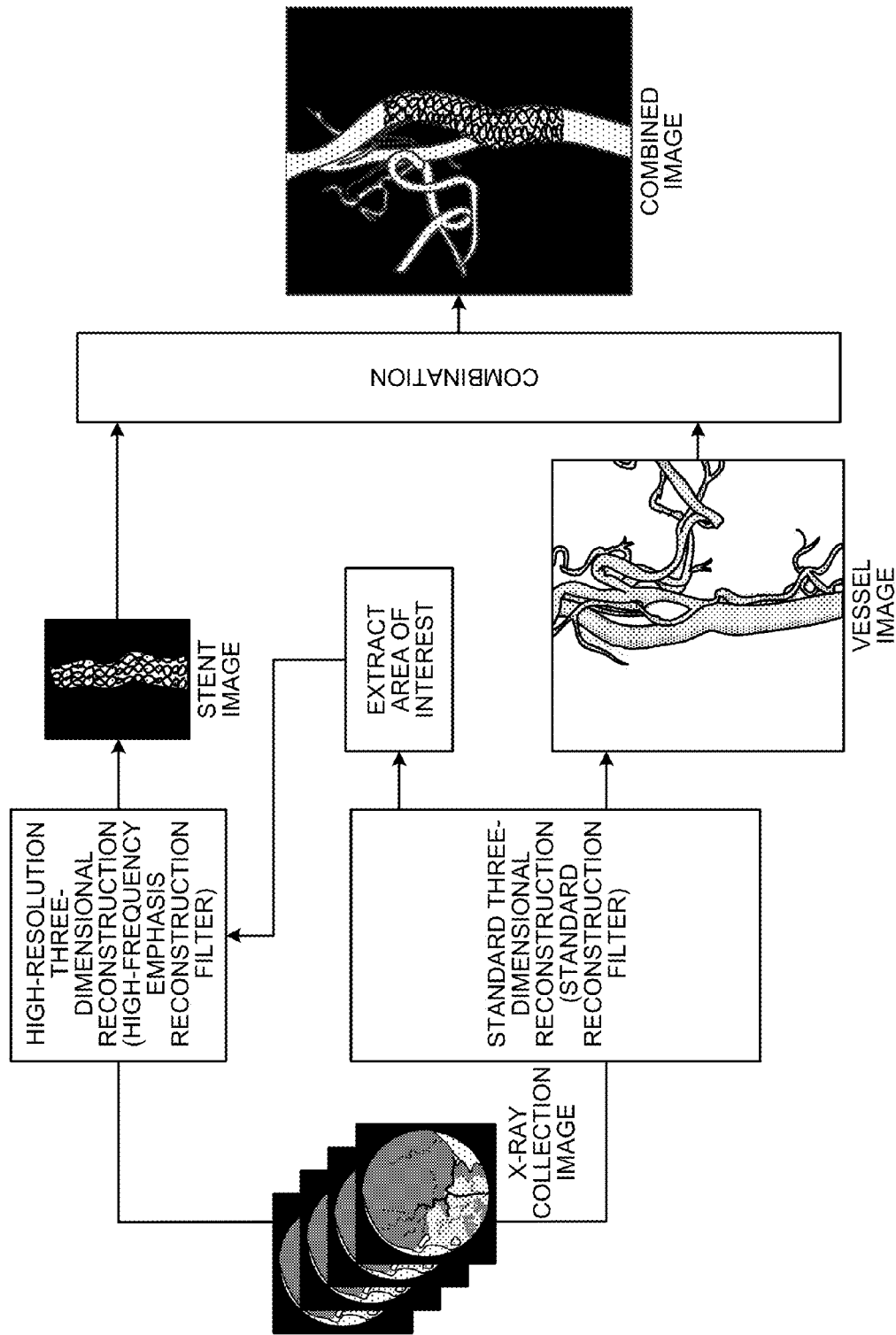

MEDICAL IMAGE PROCESSING DEVICE

CROSS-REFERENCE TO RELATED APPLICATIONS

This application is a continuation of PCT international application Ser. No. PCT/JP2011/073232 filed on Oct. 7, 2011 which designates the United States, and which claims the benefit of priority from Japanese Patent Application No. 2010-228844, filed on Oct. 8, 2010; the entire contents of which are incorporated herein by reference.

FIELD

An embodiment of the invention relates to a medical image processing device.

BACKGROUND

As one of intervention treatments (intravascular treatments), there is a coiling treatment for an aneurysm. The coiling treatment is performed only when the size of a neck at the boundary between the aneurysm and the parent vessel is less than that of the aneurysm. In the case in which the size of the neck is substantially equal to that of the aneurysm, when a coil is inserted into the aneurysm, the coil is taken off from the aneurysm and embolism occurs in a peripheral vessel.

However, in recent years, a stent for a coiling treatment has been developed. In a new treatment method using the stent, as illustrated in FIGS. 19 and 20, the stent is placed into the parent vessel and the coil is inserted through a mesh of the stent. According to the new treatment method, since the mesh of the stent prevents the coil from being taken off, it is possible to select the coiling treatment, regardless of the size of the neck. FIGS. 19 and 20 are diagrams illustrating the coiling treatment using the stent.

In the coiling treatment using the stent, it is indispensable that, after the stent is placed into the parent vessel, it comes into close contact with the parent vessel and a neck portion of the aneurysm. However, in the stent for the coiling treatment, since the diameter of a metal material forming the mesh in a cross-sectional view is very small, it is very difficult to view the metal material on a radiographic image, such as a fluoroscopic image or a captured image, and it is difficult to evaluate the degree of adhesion. Therefore, in general, a doctor checks a three-dimensional image which is reconstructed in a high spatial resolution mode from projection data (hereinafter, referred to as an X-ray collection image) and checks that the stent comes into close contact with the parent vessel and the neck portion of the aneurysm. Then, the doctor performs the coiling treatment.

However, in the related art, it is difficult to clearly observe both the stent and the vessel. When the X-ray collection image is reconstructed with high resolution, the stent is clearly drawn up to a strut, but is mixed with concave and convex portions of the surface of the vessel. As a result, there is a concern that the boundary therebetween will be unclear. On the other hand, when the X-ray collection image is reconstructed with standard resolution, stent markers are drawn in the image, but the strut is not generally drawn. For example, when the number of projection directions increases in order to solve the problems, an exposure dose increases or the injection amount of contrast medium increases.

BRIEF DESCRIPTION OF THE DRAWINGS

FIG. 4 is a diagram illustrating a reconstruction and combination process according to the first embodiment.

FIG. 5 is a diagram illustrating a reconstruction and combination process (first modification) according to the first embodiment.

DETAILED DESCRIPTION

According to an embodiment, a medical image processing device includes a first reconstruction unit, a second reconstruction unit, and an image combining unit. The first reconstruction unit generates a first reconstructed image on the basis of an X-ray collection image using a first reconstruction filter. The second reconstruction unit generates a second reconstructed image on the basis of the X-ray collection image, using a second reconstruction filter having a high-frequency emphasis effect more than that of the first reconstruction filter. The image combining unit combines the first reconstructed image with the second reconstructed image.

Hereinafter, medical image processing devices according to exemplary embodiments will be described. First, an example in which a medical image processing device, which is a medical image processing device according to a first embodiment, is incorporated into an X-ray diagnosis apparatus will be described.

(First Embodiment)
[Structure of X-Ray Diagnosis Apparatus According to First Embodiment]

Figure 1:
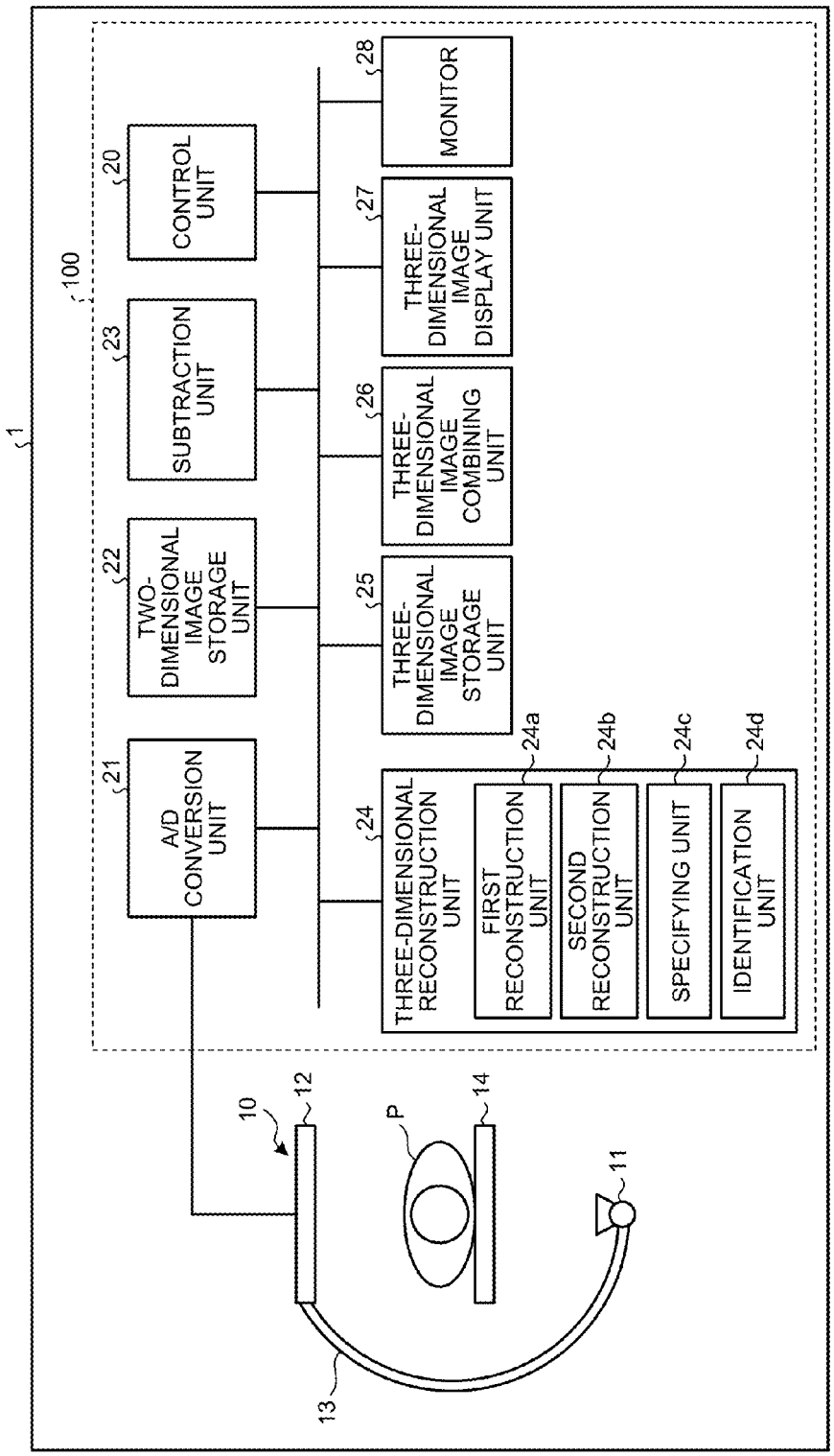
FIG. 1 is a block diagram illustrating the structure of an X-ray diagnosis apparatus according to a first embodiment.

FIG. 1 is a block diagram illustrating the structure of an X-ray diagnosis apparatus 1 according to the first embodiment. As illustrated in FIG. 1, the X-ray diagnosis apparatus 1 according to the first embodiment includes a radiographic mechanism 10 and an image processing device 100. The radiographic mechanism 10 includes an X-ray tube 11, a detector (flat panel detector (FPD)) 12, a C-shaped arm 13 (hereinafter, referred to as C-arm 13), and a bed 14. The C-arm 13 supports the X-ray tube 11 and the detector 12 and is rotated around a subject P at a high speed by a motor which is provided in the base (not illustrated), like a propeller.

The image processing device 100 includes a control unit 20, an analog/digital (A/D) conversion unit 21, a two-dimensional image storage unit 22, a subtraction unit 23, a three-dimensional reconstruction unit 24, a three-dimensional image storage unit 25, a three-dimensional image combining unit 26, a three-dimensional image display unit 27, and a monitor 28.

The control unit 20 controls the overall operation of the X-ray diagnosis apparatus 1. Specifically, the control unit 20 controls, for example, the collection of an X-ray collection image, the reconstruction of a three-dimensional image, and the display of the three-dimensional image. The A/D conversion unit 21 is connected to the detector 12, converts an analog signal input from the detector 12 into a digital signal, and stores the converted digital signal as the X-ray collection image in the two-dimensional image storage unit 22. The two-dimensional image storage unit 22 stores the X-ray collection images.

The subtraction unit 23 performs subtraction between the X-ray collection image and a non-uniformity correcting image to acquire a subtraction image. The three-dimensional reconstruction unit 24 reconstructs a three-dimensional image from the subtraction image. As illustrated in FIG. 1, the three-dimensional reconstruction unit 24 includes a first reconstruction unit 24a, a second reconstruction unit 24b, a specifying unit 24c, and an identification unit 24d, which will be described in detail below. The three-dimensional image storage unit 25 stores three-dimensional images. The three-dimensional image combining unit 26 combines the reconstructed three-dimensional images. The three-dimensional image display unit 27 displays the three-dimensional image as a volume rendering image or a multi planar reconstruction (MPR) image on the monitor 28.

[Process Performed by X-Ray Diagnosis Apparatus According to First Embodiment]

Figure 2:
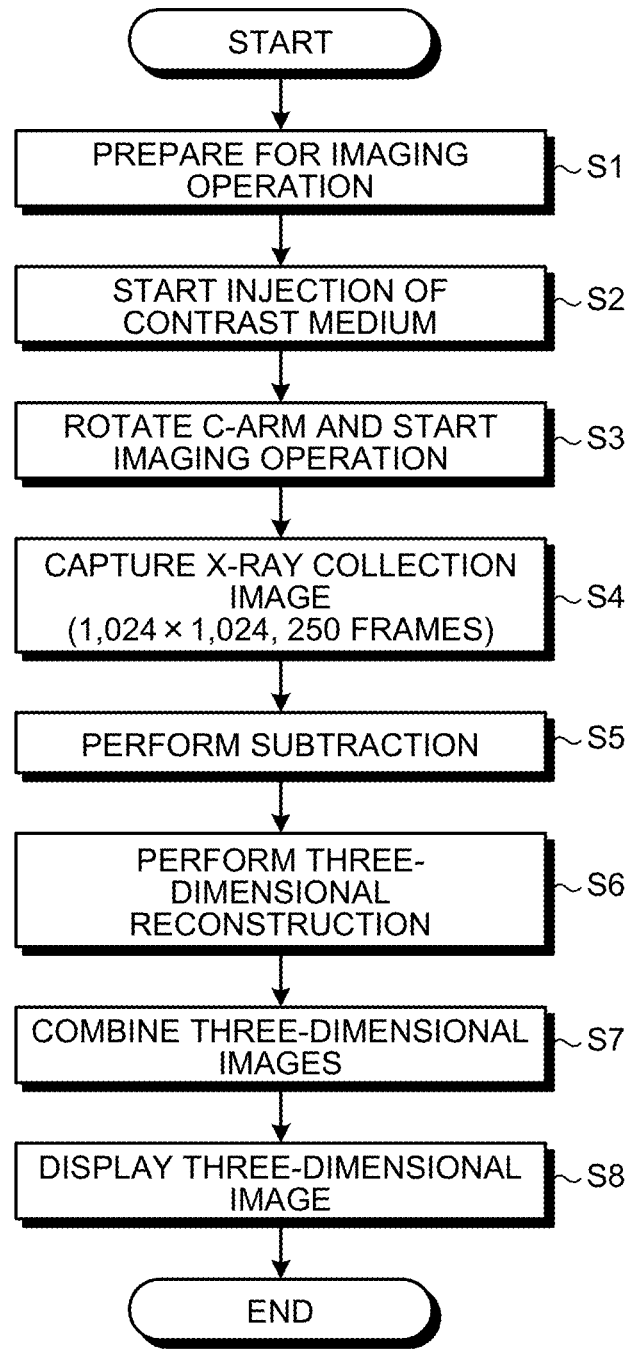
FIG. 2 is a flowchart illustrating the flow of the entire process of the X-ray diagnosis apparatus according to the first embodiment.

Next, a process performed by the X-ray diagnosis apparatus 1 according to the first embodiment will be described in detail. FIG. 2 is a flowchart illustrating the flow of the entire process of the X-ray diagnosis apparatus 1 according to the first embodiment.

As illustrated in FIG. 2, first, imaging is prepared (Step S1). Specifically, when an intervention treatment starts, the doctor inserts a catheter into a vessel. When the catheter reaches the vicinity of a desired aneurysm, the doctor places a stent so as to cover a neck at the boundary between the aneurysm and a parent vessel. The doctor performs 3D imaging in order to check whether the stent completely covers the neck, the stent comes into close contact with a vessel wall, or the stent is damaged.

In the 3D imaging, the C-arm 13 is rotated around the subject P (for example, at an angle of 180 degrees or more around the subject P) by the motor provided in the base at a high speed, like a propeller. The doctor adjusts any one of the position of the bed 14, the height of the bed 14, and the position of the C-arm 13 or a combination thereof such that the main vessel, which is a target, is within the field of view. Then, the doctor rotates the C-arm 13 to check whether there is an injury in the subject P. In this way, preparations for imaging are completed.

Then, the doctor sets a contrast medium injector to the X-ray diagnosis apparatus 1. A contrast medium with a concentration that is five to eight times lower than that of a general contrast medium used for angiography is set. The reason is that, when the contrast medium with high concentration is used, a contrast medium component negates the information of the stent.

Then, the injection of the contrast medium starts (Step S2). After a predetermined period of time (for example, 1 to 2 seconds) has elapsed from the injection of the contrast medium, the C-arm 13 is rotated and an imaging operation starts (Step S3). Then, the X-ray collection image is captured (Step S4).

For example, the C-arm 13 is rotated at an angle of 25 degrees for each second and the X-ray diagnosis apparatus 1 captures about 250 frames of X-ray collection images at an angular interval of about 0.8 degrees. The A/D conversion unit 21 converts the collected 250 frames of X-ray collection images into digital signals and stores the digital signals corresponding to 250 frames of X-ray collection images with a size of 1,024 pixels×1,024 pixels in the two-dimensional image storage unit 22.

When the X-ray collection images are stored in the two-dimensional image storage unit 22, the control unit 20 transmits the X-ray collection images stored in the two-dimensional image storage unit 22 and a non-uniformity correcting image which is collected in advance to the subtraction unit 23, and the subtraction unit 23 performs subtraction (Step S5). Specifically, the subtraction unit 23 subtracts the X-ray collection image from the corresponding non-uniformity correcting image.

Figure 3A:
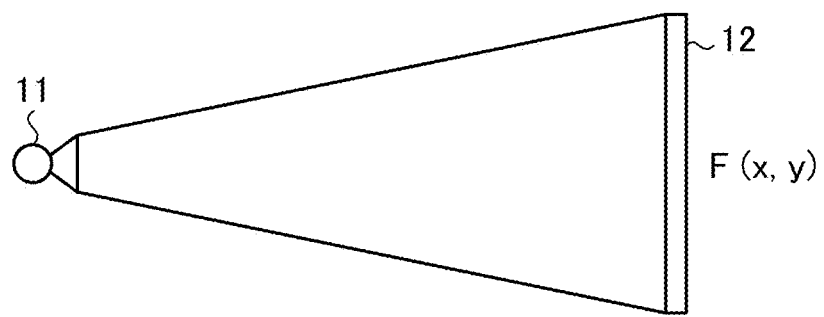
FIG. 3A is a diagram illustrating non-uniformity correction according to the first embodiment.
Figure 3B:
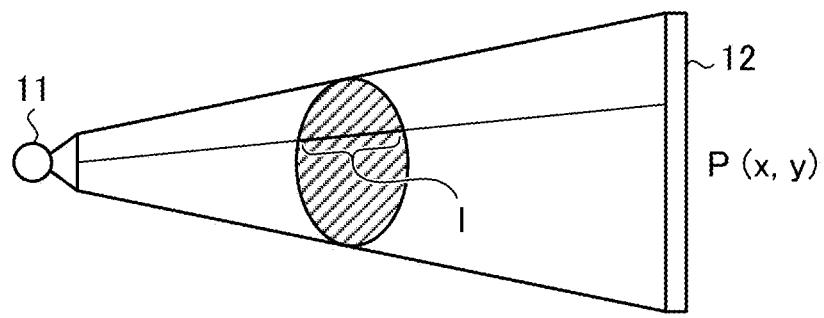
FIG. 3B is a diagram illustrating non-uniformity correction according to the first embodiment.

Next, the non-uniformity correcting image will be described. FIGS. 3A and 3B are diagrams illustrating non-uniformity correction according to the first embodiment. The non-uniformity correcting image is an image which is captured with only air between the X-ray tube 11 and the detector 12, as illustrated in FIG. 3A, and is periodically collected once every few months in a calibration process. In addition, the non-uniformity correcting image is collected for SID (Source Image Distance), FOV (Field Of View), and a radiation quality adjusting filter.

It is assumed that the image captured in the imaging environment illustrated in FIG. 3A is "F(x,y)". In addition, it is assumed that the image captured in a state in which a uniform material is interposed between the X-ray tube 11 and the detector 12 as illustrated in FIG. 3B is "P(x,y)". When the transmission distance of X-rays in the material is "1" and the X-ray absorption coefficient of the material is "μ", the following Expression 1 is established. The subtraction unit 23 obtains a subtraction image $Q_\theta(x,y)$ using the X-ray collection image, the non-uniformity correcting image, and the following Expression 2:

$$\mu l = \log_e\left(\frac{F(x, y)}{P(x, y)}\right) \qquad (1)$$

$$Q_\theta(x, y) = \log_e\left(\frac{F(x, y)}{P_\theta(x, y)}\right) \quad (2)$$

(where θ indicates an imaging angle, $P_\theta(x,y)$ is the X-ray collection image of the subject at the imaging angle θ, $F(x,y)$ is a non-uniformity correcting image, and $Q_\theta(x,y)$ is a subtraction image at the imaging angle θ).

When the subtraction unit 23 performs subtraction, the control unit 20 transmits the subtraction image $Q_\theta(x,y)$ to the three-dimensional reconstruction unit 24 and the three-dimensional reconstruction unit 24 performs reconstruction (Step S6). In the first embodiment, for convenience of explanation, the "subtraction image $Q_\theta(x,y)$" is referred to as an "X-ray projection image".

The three-dimensional reconstruction unit 24 and the three-dimensional image combining unit 26 according to the first embodiment perform two kinds of reconstructions, combine two kinds of reconstructed images obtained by two kinds of reconstructions, and output a combined image. Specifically, first, the first reconstruction unit 24a of the three-dimensional reconstruction unit 24 generates a first reconstructed image on the basis of the X-ray collection image using a first reconstruction filter. The second reconstruction unit 24b of the three-dimensional reconstruction unit 24 generates a second reconstructed image on the basis of the X-ray collection image using a second reconstruction filter. The second reconstruction filter has a high-frequency emphasis effect more than that of the first reconstruction filter. The three-dimensional image combining unit 26 combines the first reconstructed image with the second reconstructed image. In the first embodiment (except for the following modifications 1 and 2), the processes of the specifying unit 24c and the identification unit 24d are not performed. Therefore, the three-dimensional reconstruction unit 24 may not include each of the units.

FIG. 4 is a diagram illustrating a reconstruction and combination process according to the first embodiment. As illustrated in FIG. 4, the three-dimensional reconstruction unit 24 performs a first reconstruction using a standard reconstruction filter (hereinafter, appropriately referred to as a "standard reconstruction filter") and a second reconstruction using a reconstruction filter (hereinafter, appropriately referred to as a "high-frequency emphasis reconstruction filter") with a great high-frequency emphasis effect on the X-ray projection image transmitted from the subtraction unit 23. Each reconstruction filter may be a combination of two kinds of reconstruction filters such that one of, for example, a Ramachandran reconstruction filter, a Smoothed Shepp & Logan reconstruction filter, a Shepp & Logan reconstruction filter has a high-frequency emphasis effect more than that of another reconstruction filter, which will be described in detail below with reference to FIG. 16.

When the first reconstruction is performed using the standard reconstruction filter, as illustrated in FIG. 4, the first reconstruction unit 24a obtains a reconstructed image ("vessel image" illustrated in FIG. 4) from which the vessels are extracted. Since the reconstructed image is reconstructed by the standard reconstruction filter, most of the stent is not drawn in the reconstructed image. The reconstructed image is formed such that concave and convex portions of the surface of the vessels are not excessively emphasized and it is easy to observe the overall structure of the vessels.

When the second reconstruction is performed using the high-frequency emphasis reconstruction filter, the second reconstruction unit 24b obtains a reconstructed image ("stent image" illustrated in FIG. 4) from which the stent is clearly extracted up to a strut, as illustrated in FIG. 4. FIG. 4 illustrates a stent image from which only a stent portion is extracted. However, in practice, an image from which both the stent and the vessels are extracted is used. The stent is made of metal and has a large computed tomography (CT) value. The second reconstruction unit 24b adjusts a window width or a window level for the reconstructed image to increase the density of the image of the stent and decrease the density of the image of the vessel. For example, the window width is the range of a density value allocated to the range from the maximum brightness to the minimum brightness and the window level is, for example, an intermediate density value of the window width.

FIG. 4 illustrates an example in which two kinds of reconstructions are performed in parallel to each other, but the embodiment is not limited thereto. For example, after the reconstruction using the high-frequency emphasis reconstruction filter is performed, the reconstruction using the standard reconstruction filter may be performed. Alternatively, after the reconstruction using the standard reconstruction filter is performed, the reconstruction using the high-frequency emphasis reconstruction filter may be performed.

Returning to FIG. 2, when two kinds of reconstructed images are stored in the three-dimensional image storage unit 25, the control unit 20 transmits the two kinds of reconstructed images stored in the three-dimensional image storage unit 25 to the three-dimensional image combining unit 26. Then, the three-dimensional image combining unit 26 combines the two kinds of reconstructed images. Specifically, the three-dimensional image combining unit 26 combines the reconstructed image obtained by the first reconstruction with the reconstructed image obtained by the second reconstruction and outputs the combined image. In the combined image, the image of the stent and the image of the vessel overlap each other. The reconstructed image in which the stent is not drawn and the overall structure of the vessels is drawn so as to be easily observed and the reconstructed image in which only the stent is clearly drawn and the vessel is drawn with low density overlap each other in the combined image. As a result, as illustrated in FIG. 4, the overall structure of the vessels can be observed from the combined image and the stent is clearly drawn in the combined image.

When two kinds of reconstructed images are combined with each other, the control unit 20 transmits the combined three-dimensional image to the three-dimensional image display unit 27, and the three-dimensional image display unit 27 displays the combined three-dimensional image as a volume rendering image or an MPR image on the monitor 28.

In this embodiment, it is premised that various kinds of correction are not performed in the reconstruction process. However, the embodiment is not limited thereto. For example, scattered ray correction, beam hardening correction, and ring correction may be performed.

In this way, according to the first embodiment, both the stent and the vessels can be clearly observed. That is, according to the first embodiment, two kinds of reconstructions are performed on the X-ray collection image and the images are combined with each other. In this way, it is possible to obtain an image from which the overall structure of the vessels can be observed and in which the stent is clearly drawn. In particular, it is possible to clearly observe both the stent and the vessels without increasing the number of projection directions.

(First Modification)

A first modification of the first embodiment will be described below. FIG. 5 is a diagram illustrating a reconstruction and combination process (first modification) according to the first embodiment. The difference from the reconstruction and combination process described with reference to FIG. 4 will be mainly described. As illustrated in FIG. 5, the three-dimensional reconstruction unit 24 according to the first modification extracts the area of interest using the reconstructed image which is obtained by the first reconstruction using the standard reconstruction filter and performs the second reconstruction using the high-frequency emphasis reconstruction filter on only the extracted area of interest.

The area of interest may be determined by instructions from the operator. However, a method of automatically extracting the area of interest from the reconstructed image will be described. Specifically, the three-dimensional reconstruction unit 24 according to the first modification performs the processes of the specifying unit 24c and the identification unit 24d. The specifying unit 24c performs threshold processing on the reconstructed image obtained by the first reconstruction to specify stent markers. The identification unit 24d identifies the area of interest surrounded by the stent markers in the reconstructed image obtained by the first reconstruction. The second reconstruction unit 24b applies the high-frequency emphasis reconstruction filter only to the area of interest identified by the identification unit 24d in the X-ray collection image, and generates a reconstructed image only for the area of interest.

Figure 6:
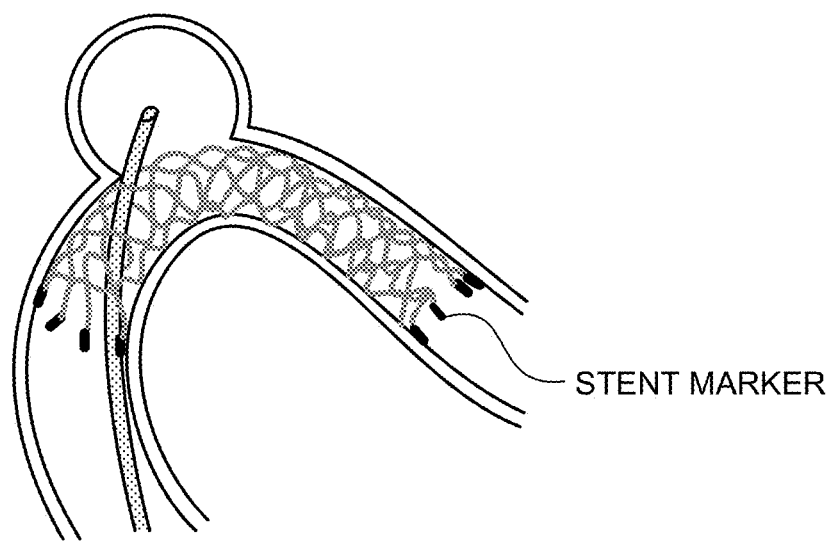
FIG. 6 is a diagram illustrating stent markers according to the first embodiment.

FIG. 6 is a diagram illustrating the stent markers according to the first embodiment. For example, the specifying unit 24c according to the first modification performs image processing on the reconstructed image obtained by the first reconstruction to specify the stent markers. As illustrated in FIG. 6, the stent markers are positioned at both ends of the stent (for example, four stent markers are provided at each end). The stent marker has high absorptance and a CT value that is as large as a portion of the stent marker. Therefore, the specifying unit 24c can perform, for example, threshold processing to specify the stent markers. The identification unit 24d further extracts an area which is surrounded by the stent markers specified by the specifying unit 24c, thereby identifying the area of interest, that is, a stent area. Similarly, a metal prosthetic tooth has a large CT value, but the volume of the metal prosthetic tooth is significantly larger than that of the stent marker. Therefore, when the volume is measured, the prosthetic tooth can be excluded.

Since the second reconstruction unit 24b performs the second reconstruction on only the stent area using the high-frequency emphasis reconstruction filter, only the stent portion is exactly extracted and a stent image in which the stent is clearly drawn is obtained, as illustrated in FIG. 5. As such, according to the first modification, it is easy to adjust the window width or the window level. In addition, since a second reconstruction area is small, the time required for reconstruction is reduced. Then, the three-dimensional image combining unit 26 combines the reconstructed image obtained by the first reconstruction with the reconstructed image obtained by the second reconstruction, similarly to the first embodiment described with reference to FIG. 4.

(Second Modification)

Figure 7:
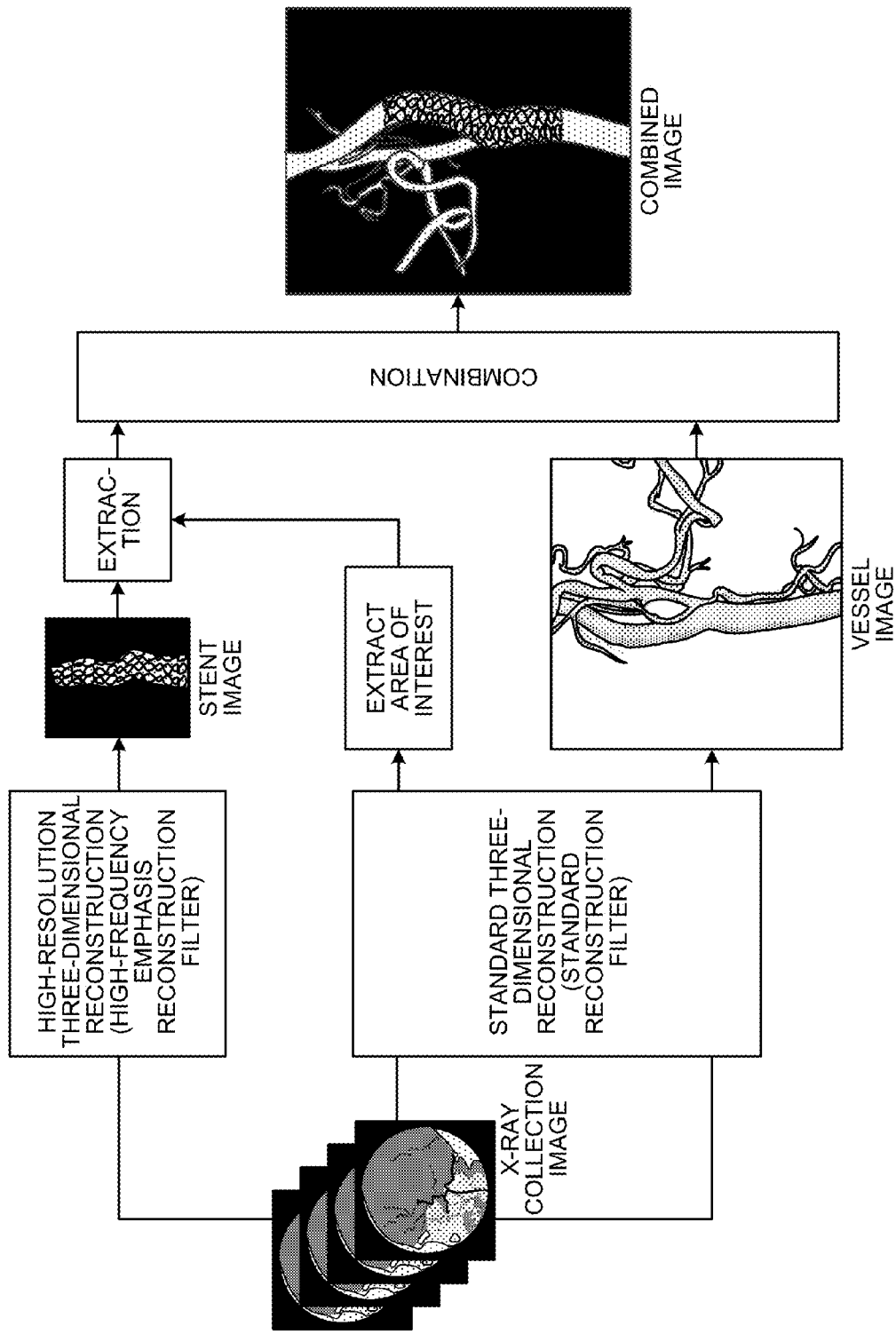
FIG. 7 is a diagram illustrating a reconstruction and combination process (second modification) according to the first embodiment.

A second modification of the first embodiment will be described below. FIG. 7 is a diagram illustrating a reconstruction and combination process (second modification) according to the first embodiment. The difference from the reconstruction and combination process described with reference to FIG. 5 will be mainly described. In the second modification, the extraction of the area of interest is performed as a post-process of the second reconstruction using the high-frequency emphasis reconstruction filter.

That is, the second reconstruction unit 24b according to the second modification performs the second reconstruction using the high-frequency emphasis reconstruction filter on the entire X-ray projection image, similarly to the first embodiment described with reference to FIG. 4. The specifying unit 24c performs threshold processing on the reconstructed image obtained by the first reconstruction to specify the stent markers, and the identification unit 24d identifies the area of interest surrounded by the stent markers in the reconstructed image obtained by the second reconstruction. That is, the identification unit 24d cuts out the stent area from the reconstructed image obtained by the second reconstruction, using the information of the area of interest which is obtained from the reconstructed image obtained by the first reconstruction. Then, the three-dimensional image combining unit 26 combines the reconstructed image obtained by the first reconstruction with the reconstructed image which is obtained by the second reconstruction and from only the stent area is cut out. As such, in the second modification, it is also easy to adjust the window width or the window level.

(Second Embodiment)

Next, a second embodiment will be described. It is assumed that the second embodiment is implemented by the same X-ray diagnosis apparatus 1 as the X-ray diagnosis apparatus 1 according to the first embodiment. The difference between the second embodiment and the first embodiment is as follows. In the first embodiment, two kinds of reconstructions are performed on the image after the contrast medium is injected. However, in the second embodiment, an image is collected before and after the contrast medium is injected and two kinds of reconstructions are performed using the subtraction image and the image before the contrast medium is injected. Next, the difference from the first embodiment will be mainly described.

Figure 8:
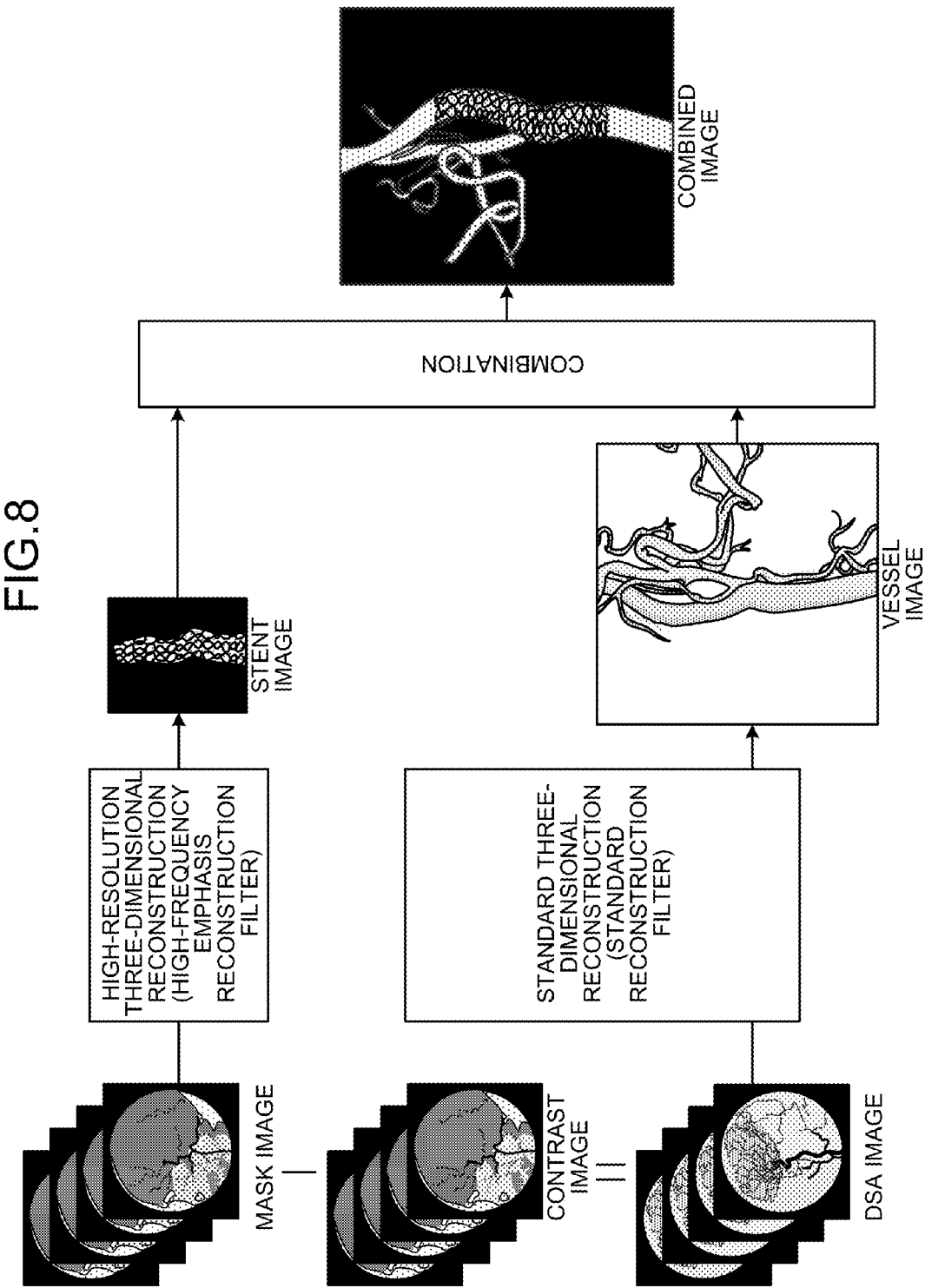
FIG. 8 is a diagram illustrating a reconstruction and combination process according to a second embodiment.

FIG. 8 is a diagram illustrating a reconstruction and combination process according to the second embodiment. In the second embodiment, a subtraction unit 23 performs subtraction between an image (hereinafter, appropriately referred to as a "mask image") before a contrast medium is injected and a non-uniformity correcting image and also performs subtraction between the mask image and an image (hereinafter, appropriately referred to as a "contrast image") after the contrast medium is injected. Hereinafter, the image obtained by the former subtraction is appropriately referred to as an X-ray projection image and the image obtained by the latter subtraction is appropriately referred to as a digital subtraction angiography (DSA) image. Then, the subtraction unit 23 according to the second embodiment transmits the X-ray projection image and the DSA image to a three-dimensional reconstruction unit 24.

The three-dimensional reconstruction unit 24 according to the second embodiment performs a first reconstruction using a standard reconstruction filter on the DSA image transmitted from the subtraction unit 23, and performs a second reconstruction using a high-frequency emphasis reconstruction filter on the X-ray projection image. That is, a first reconstruction unit 24a performs the first reconstruction on the DSA image using the standard reconstruction filter and a second reconstruction unit 24b performs the second reconstruction on the X-ray projection image using the high-frequency emphasis reconstruction filter.

In this case, since the X-ray projection image is obtained before the contrast medium is injected, the vessel is not drawn in the X-ray projection image. In the reconstructed image obtained by the second reconstruction, the vessel is not drawn and only the stent is clearly drawn. Therefore, according to the second embodiment, it is easy to adjust the window width or the window level. Since the DSA image is a subtraction image before and after the contrast medium is injected, only the vessel is drawn in the DSA image. Then, similarly to the first embodiment, a three-dimensional image combining unit 26 combines the reconstructed image obtained by the first reconstruction with the reconstructed image obtained by the second reconstruction.

Therefore, according to the second embodiment, it is possible to clearly observe both the stent and the vessels. That is, according to the second embodiment, two kinds of reconstructions are performed on the image from which only the stent is extracted and the image from which only the vessel is extracted and the images are combined with each other. Therefore, unnecessary overlap, such as overlap between one of the two images and the image of the stent or the vessels which are unclearly drawn, does not occur and it is possible to clearly observe both the stent and the vessels.

(First Modification)

Figure 9:
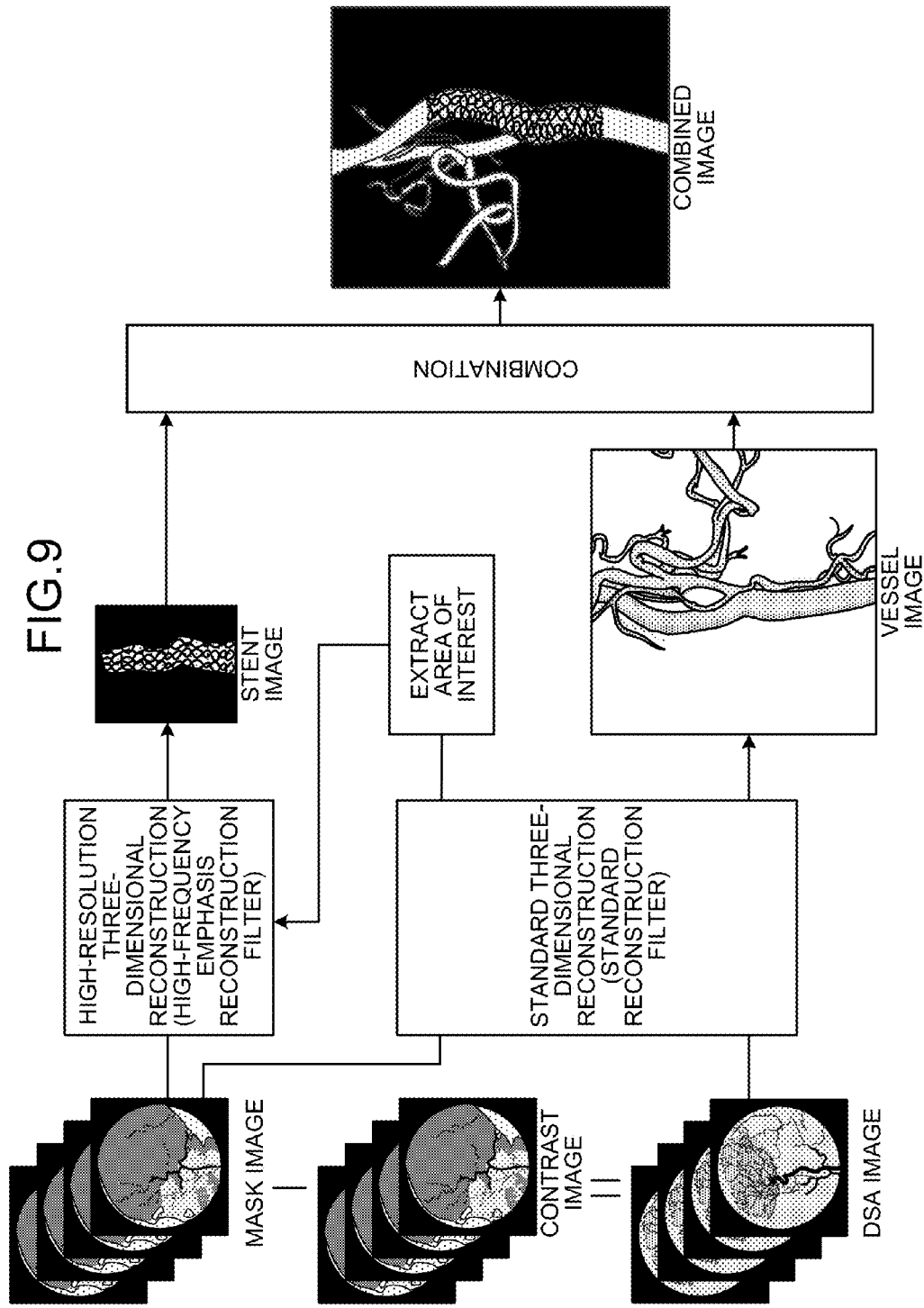
FIG. 9 is a diagram illustrating a reconstruction and combination process (first modification) according to the second embodiment.

A first modification of the second embodiment will be described. FIG. 9 is a diagram illustrating a reconstruction and combination process (first modification) according to the second embodiment. The difference from the reconstruction and combination process described with reference to FIG. 8 will be mainly described below. As illustrated in FIG. 9, the three-dimensional reconstruction unit 24 according to the first modification performs the first reconstruction using the standard reconstruction filter on the X-ray projection image in addition to the DSA image. That is, as described above, no vessel is drawn in the X-ray projection image. Therefore, the specifying unit 24c according to the first modification performs the first reconstruction using the standard reconstruction filter on the X-ray projection image and performs image processing on the reconstructed image, thereby specifying the stent markers.

The other processes are the same as those in the first modification of the first embodiment. The second reconstruction unit 24b performs the second reconstruction on only the stent area using the high-frequency emphasis reconstruction filter. Therefore, as illustrated in FIG. 9, only a stent portion is exactly extracted and a stent image in which the stent is clearly drawn is obtained. As such, according to the first modification of the second embodiment, it is unnecessary to adjust the window width or the window level. In addition, since the second reconstruction area is small, the time required for reconstruction is reduced.

Similarly to the first modification of the first embodiment, the area of interest may be determined by instructions from the operator.

(Second Modification)

Figure 10:
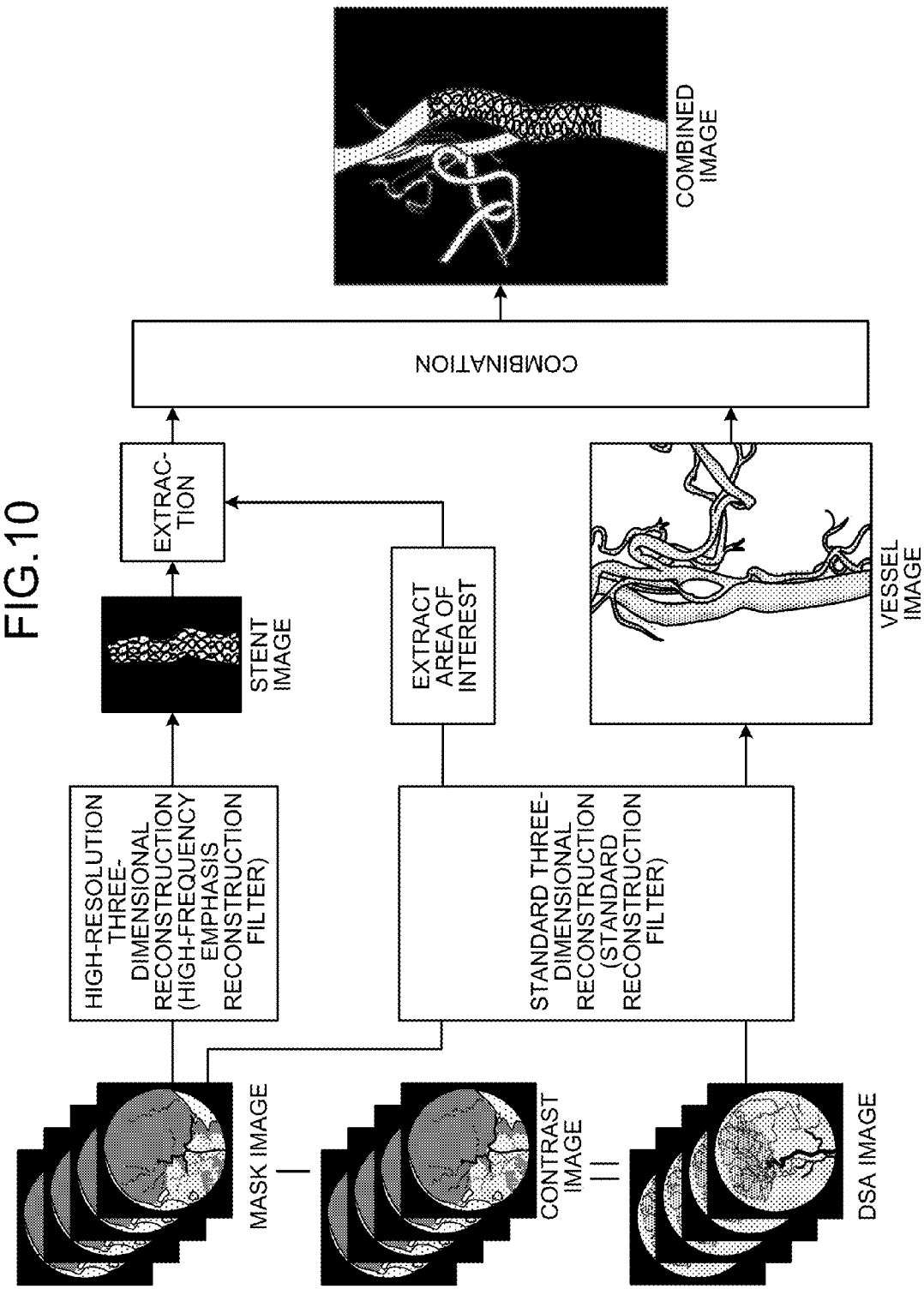
FIG. 10 is a diagram illustrating a reconstruction and combination process (second modification) according to the second embodiment.

A second modification of the second embodiment will be described. FIG. 10 is a diagram illustrating a reconstruction and combination process (second modification) according to the second embodiment. The difference from the reconstruction and combination process described with reference to FIG. 9 will be mainly described below. In the second modification, the extraction of the area of interest is performed as a post-process of the second reconstruction using the high-frequency emphasis reconstruction filter.

That is, the second reconstruction unit 24b according to the second modification performs the second reconstruction using the high-frequency emphasis reconstruction filter on the entire X-ray projection image, similarly to the second embodiment described with reference to FIG. 7. The specifying unit 24c performs the first reconstruction on the X-ray projection image using the standard reconstruction filter, and performs threshold processing on the reconstructed image to specify the stent markers. The identification unit 24d identifies the area of interest surrounded by the stent markers in the reconstructed image obtained by the second reconstruction. That is, the identification unit 24d cuts out the stent area from the reconstructed image obtained by the second reconstruction, using the information of the area of interest which is obtained from the reconstructed image obtained by the first reconstruction. Then, the three-dimensional image combining unit 26 combines the reconstructed image obtained by the first reconstruction with the reconstructed image which is obtained by the second reconstruction and from only the stent area is cut out. As such, in the second modification, it is also easy to adjust the window width or the window level.

(Third Embodiment)

Next, a third embodiment will be described. Before the third embodiment is described in detail, a reconstruction filter will be described. In the first embodiment and the second embodiment, two kinds of reconstruction filters may be appropriately combined with each other such that, among the Ramachandran reconstruction filter, the Smoothed Shepp & Logan reconstruction filter, and the Shepp & Logan reconstruction filter, one reconstruction filter has a high-frequency emphasis effect more than that of another reconstruction filter. In the following description, when a reconstruction filter has a relatively great high-frequency emphasis effect, it is referred to as a "sharp convolution filter" and, when a reconstruction filter has a less high-frequency emphasis, it is referred to as a "smooth convolution filter".

In the first embodiment and the second embodiment, two kinds of reconstructions are performed by the "sharp convolution filter" and the "smooth convolution filter". However, in the third embodiment, a method of performing a reducing process or a low-pass filtering process as a pre-process will be described.

That is, when the reducing process is performed as the pre-process and the "sharp convolution filter" is used as the reconstruction filter, the same effect as that when the "smooth convolution filter" is used is obtained as the entire result including the result of the reducing process. Similarly, when the low-pass filtering process is performed as the pre-process and the "sharp convolution filter" is used as the reconstruction filter, the same effect as that when the "smooth convolution filter" is used is obtained as the entire result including the result of the low-pass filtering process. Therefore, in the third embodiment, a first reconstruction unit 24a of a three-dimensional reconstruction unit 24 performs the reducing process or the low-pass filtering process in advance.

Figure 11:
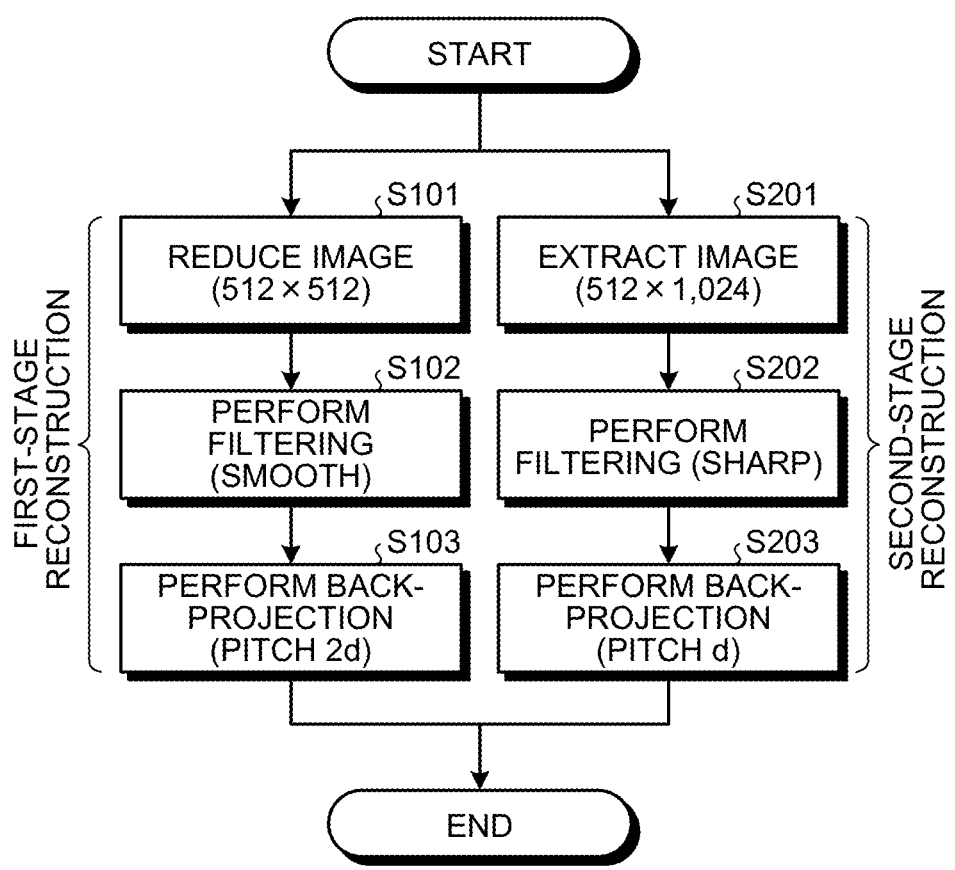
FIG. 11 is a flowchart illustrating the flow of a reconstruction process according to a third embodiment.

Next, a reconstruction and combination process according to the third embodiment will be described in detail. The three-dimensional reconstruction unit 24 according to the third embodiment performs reconstruction in two stages, similarly to the first embodiment and the second embodiment. FIG. 11 is a flowchart illustrating the flow of a reconstruction process according to the third embodiment. As illustrated in FIG. 11, the three-dimensional reconstruction unit 24 performs a "first-stage reconstruction" and a "second-stage reconstruction". In FIG. 11, the three-dimensional reconstruction unit 24 performs the "first-stage reconstruction" and the "second-stage reconstruction" in parallel, but the embodiment is not limited thereto. For example, after the "first-stage reconstruction" is performed, the "second-stage reconstruction" may be performed. Alternatively, after the "second-stage reconstruction" is performed, the "first-stage reconstruction" may be performed.

Figure 12:
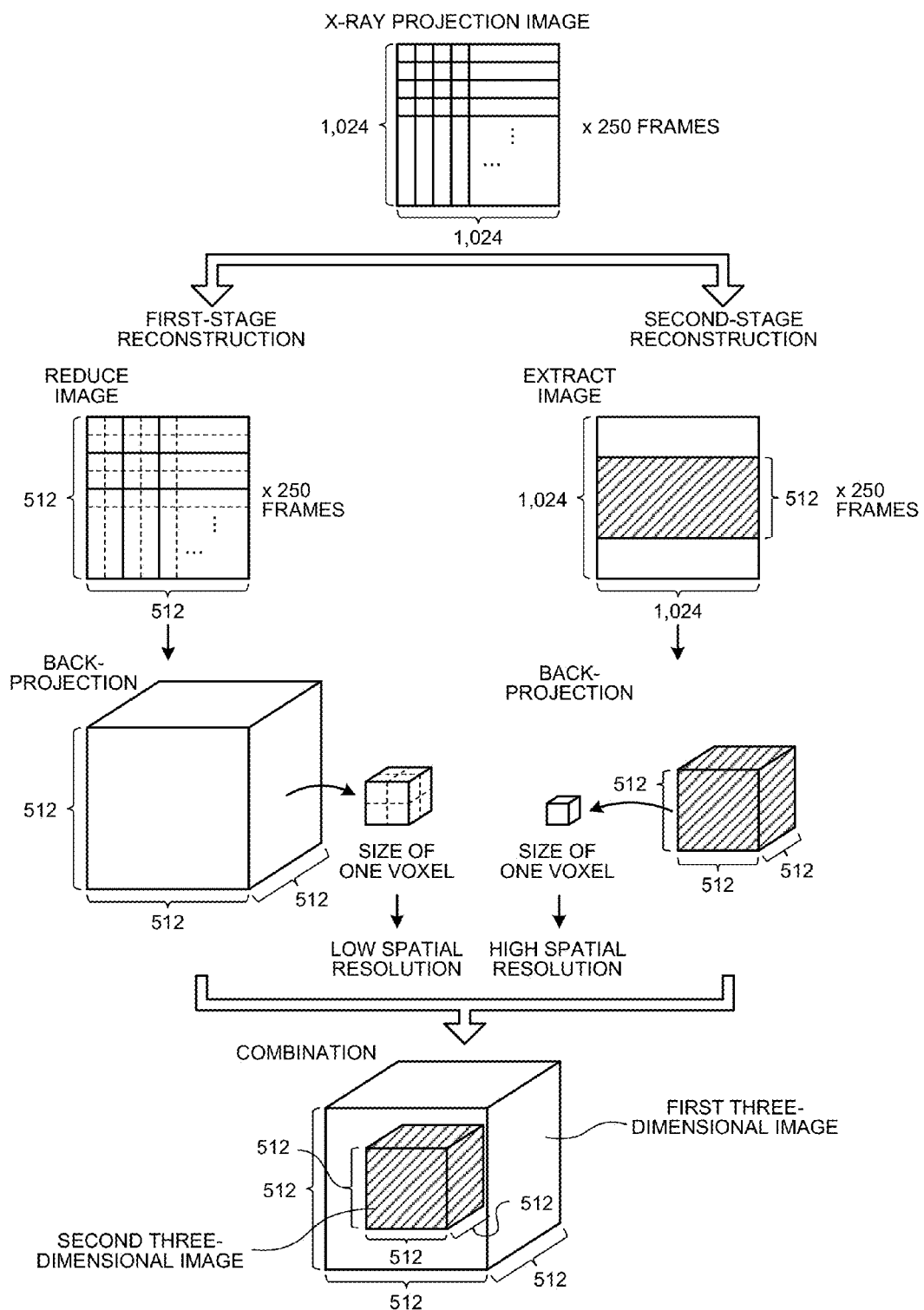
FIG. 12 is a diagram illustrating the reconstruction process according to the third embodiment.

Next, each of the "first-stage reconstruction" and the "second-stage reconstruction" will be described with reference to FIGS. 11 to 18. FIG. 12 is a diagram illustrating the reconstruction process according to the third embodiment.

The "first-stage reconstruction" will be described. First, the three-dimensional reconstruction unit 24 (first reconstruction unit 24a) reduces an X-ray projection image (Step S101). For example, as illustrated in FIG. 12, the three-dimensional reconstruction unit 24 (first reconstruction unit 24a) reduces the X-ray projection image with a size of 1,024 pixels×1,024 pixels such that the size of a reduced pixel corresponds to that of four pixels before reduction. Then, the reduced X-ray projection image corresponds to 250 frames of X-ray projection images with a size of 512 pixels×512 pixels.

Then, the three-dimensional reconstruction unit 24 (first reconstruction unit 24a) performs reconstruction on 250 frames of the reduced X-ray projection images with a size of 512 pixels×512 pixels using the smooth convolution filter, such as a Smoothed Shepp & Logan filter (Step S102).

Then, the three-dimensional reconstruction unit 24 (first reconstruction unit 24a) performs a back-projection process to generate a first three-dimensional image and stores the generated first three-dimensional image in a three-dimensional image storage unit 25 (Step S103).

Next, the "second-stage reconstruction" will be described. First, the three-dimensional reconstruction unit (second reconstruction unit 24b) extracts a portion of the X-ray projection image (Step S201). For example, as illustrated in FIG. 12, the three-dimensional reconstruction unit 24 (second reconstruction unit 24b) extracts an X-ray projection image with a size of 512 pixels×1,024 pixels from a subtraction image with a size of 1,024 pixels×1,024 pixels. As a result, the three-dimensional reconstruction unit 24 (second reconstruction unit 24b) acquires 250 frames of X-ray projection images with a size of 512 pixels×1,024 pixels.

Then, the three-dimensional reconstruction unit 24 (second reconstruction unit 24b) performs a reconstruction process on the extracted X-ray projection image. In this embodiment, a filtered back-projection method proposed by Feldkamp, et al. is used as an example of the reconstruction method. The three-dimensional reconstruction unit 24 (second reconstruction unit 24b) performs reconstruction on 250 frames of the extracted X-ray projection images with a size of 512 pixels×1,024 pixels, using the sharp convolution filter, such as the Shepp & Logan filter or the Ramachandran filter (Step S202).

Then, the three-dimensional reconstruction unit 24 (second reconstruction unit 24b) performs the back-projection process to generate a second three-dimensional image and stores the generated second three-dimensional image in the three-dimensional image storage unit 25 (Step S203).

Figure 13:
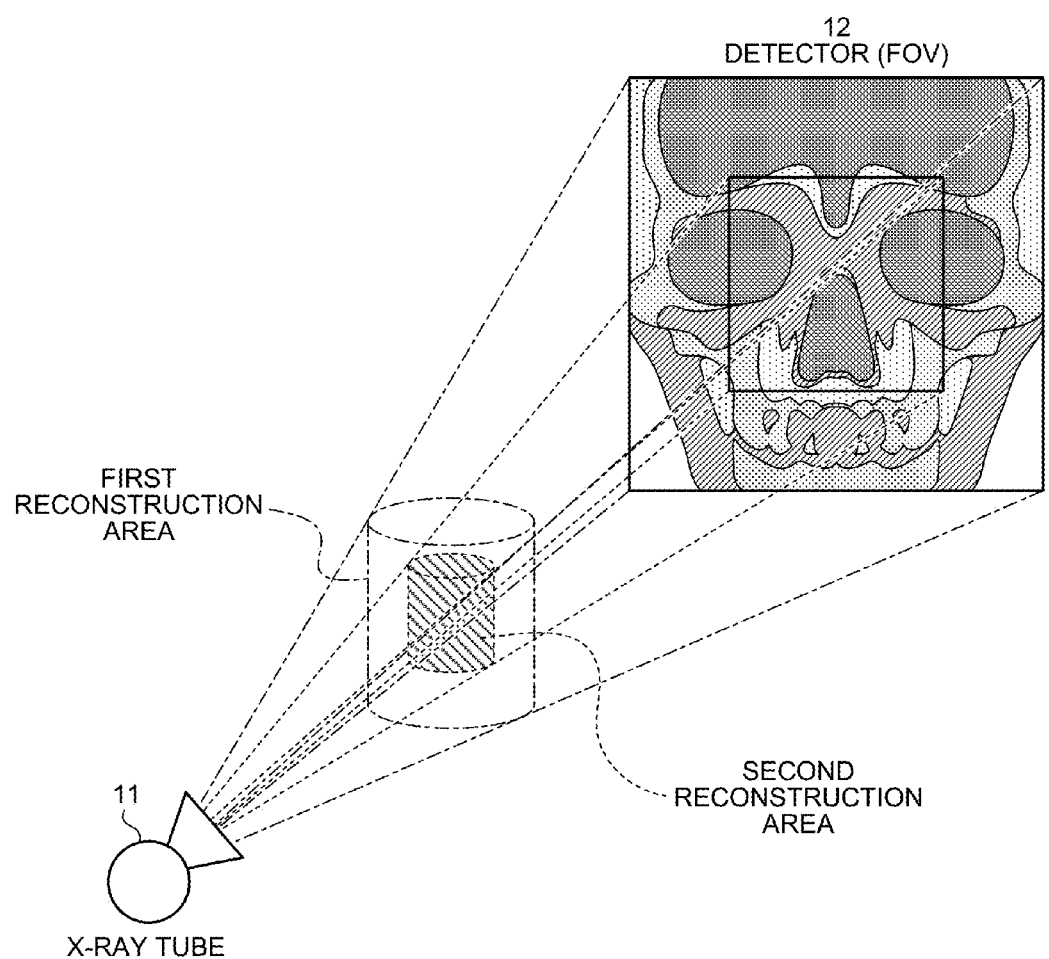
FIG. 13 is a diagram illustrating a reconstruction area according to the third embodiment.
Figure 14:
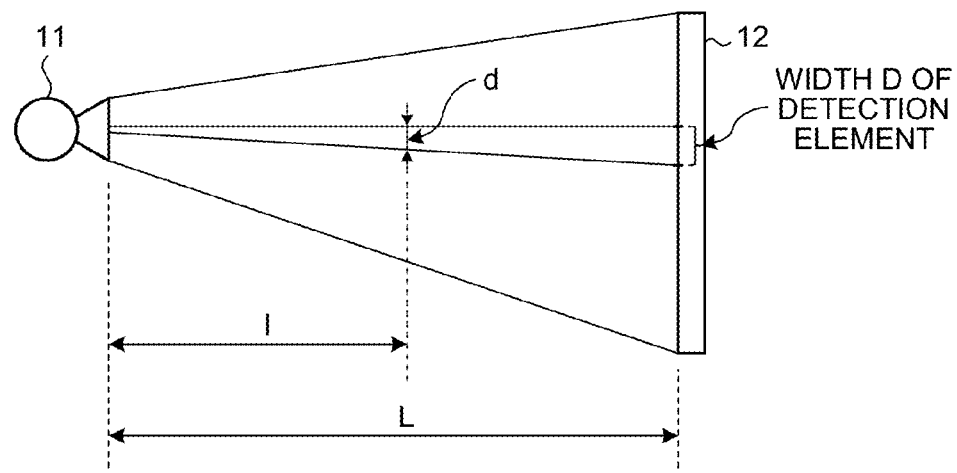
FIG. 14 is a diagram illustrating a discrete interval according to the third embodiment.
Figure 15:
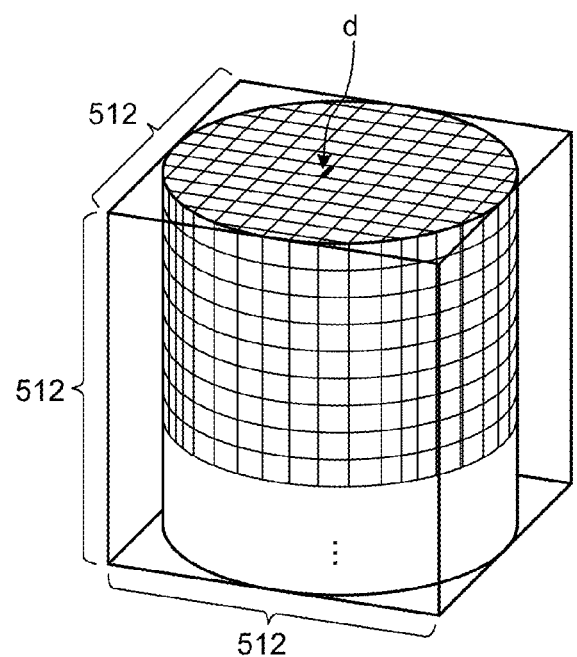
FIG. 15 is a diagram illustrating the discrete interval according to the third embodiment.

Next, a reconstruction area reconstructed by the three-dimensional reconstruction unit 24 will be described. FIG. 13 is a diagram illustrating the reconstruction area according to the third embodiment. FIGS. 14 and 15 are diagrams illustrating a discrete interval according to the third embodiment.

First, the second reconstruction area is defined as a cylinder which is inscribed in the overlap between the X-ray tube 11 and a central area (FOV/2×FOV/2) of the FOV of the detector 12 when a quadrangular pyramid including the X-ray tube 11 and the central area of the FOV of the detector 12 is defined in all directions, as illustrated in FIG. 13. In addition, as illustrated in FIGS. 14 and 15, for example, the inside of the cylinder is three-dimensionally discretized with a length "d" at the center of a reconstruction area which is projected with the width "D" of one detection element of the detector 12. When the distance between the X-ray tube 11 and the detector 12 is "L" and the distance between the X-ray tube 11 and the center of the reconstruction area is "l", the length "d" is represented by the following Expression 3:

$$d = \frac{D \cdot l}{L} \quad (3)$$

As such, the three-dimensional reconstruction unit 24 generates, as the second three-dimensional image, the data of a discrete point with a size of 512×512×512 voxels which is three-dimensionally discretized with the length "d". Since the second three-dimensional image is reconstructed from the X-ray projection image with a size of 512 pixels×1,024 pixels, the three-dimensional reconstruction unit 24 can generate the data of the inside of a cube with a size of 512×512×512 voxels, which is the data of the outside of the cylinder, in addition to the data of the inside of the cylinder illustrated in FIG. 15. In this embodiment, an example of the discrete interval is given, but the discrete interval varies depending on devices or manufacturers. Therefore, basically, a discrete interval which is defined by a device may be used.

The first reconstruction area is defined as a cylinder which is inscribed in the overlap between the X-ray tube 11 and the area (FOV/2×FOV/2) of the FOV of the detector 12 when the quadrangular pyramid including the X-ray tube 11 and the area of the FOV of the detector 12 is defined in all directions, as illustrated in FIG. 13. In addition, the inside of the cylinder is three-dimensionally discretized with a length "2d". As such, the three-dimensional reconstruction unit 24 generates, as the first three-dimensional image, the data of a discrete point with a size of 512×512×512 voxels which is three-dimensionally discretized with the length "2d".

Figure 16:
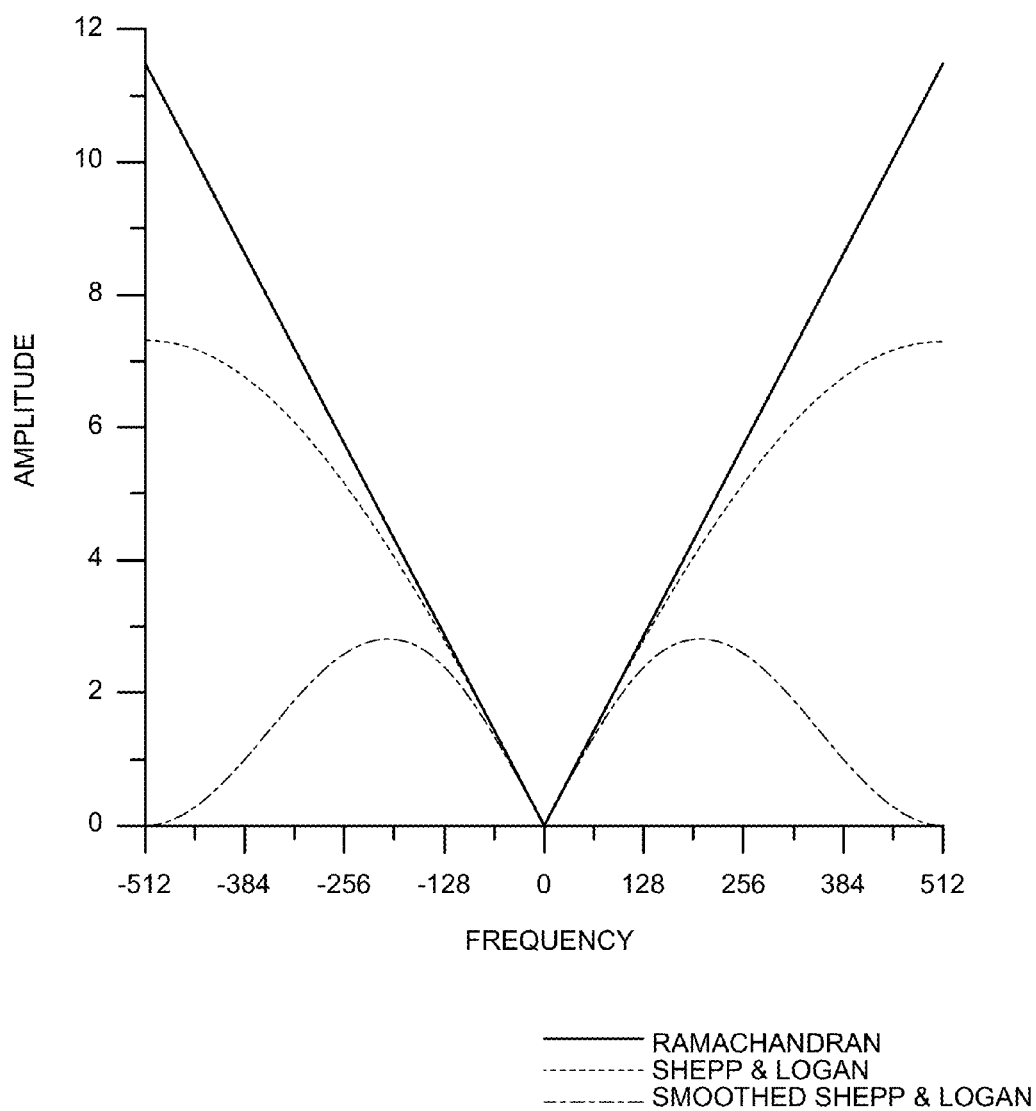
FIG. 16 is a diagram illustrating a convolution filter according to the third embodiment.

Next, the convolution filter will be described. FIG. 16 is a diagram illustrating the convolution filter according to the third embodiment. In general, examples of the convolution filter include a "smooth" convolution filter used in the "first-stage reconstruction" and a "sharp" convolution filter used in the "second-stage reconstruction". The high-frequency emphasis effect of the "sharp" convolution filter is more than that of the "smooth" convolution filter.

For example, FIG. 16 illustrates three kinds of convolution filters. The three kinds of convolution filters are the Ramachandran convolution filter, which is the "sharpest" convolution filter, the Smoothed Shepp & Logan convolution filter, which is the "smoothest" convolution filter, and the Shepp & Logan convolution filter, which is an intermediate convolution filter.

In general, when the "sharp" convolution filter is used for reconstruction, a high frequency is emphasized. As a result, it is easy to obtain a clear image. That is, the X-ray diagnosis apparatus 1 according to the third embodiment performs different processes, such as the "first-stage reconstruction" and the "second-stage reconstruction", extracts a clear image in the area of interest, without changing the convolution filters applied to the first-stage reconstruction and the second-stage reconstruction, and prevents the deterioration of the image of a peripheral portion.

In this way, as illustrated in FIG. 12, the first three-dimensional image and the second three-dimensional image are generated. As can be seen from the comparison between the first three-dimensional image generated by the "first-stage reconstruction" and the second three-dimensional image generated by the "second-stage reconstruction", the size of a voxel of the second three-dimensional image is less than that of a voxel of the first three-dimensional image and the spatial resolution of the second three-dimensional image is higher than that of the first three-dimensional image. That is, since the second three-dimensional image is generated from the subtraction image which is extracted without being reduced, the size of a voxel of the second three-dimensional image maintains high spatial resolution when the X-ray collection image is collected. In addition, since the first three-dimensional image is generated from the reduced subtraction image, the size of a voxel of the first three-dimensional image is less than the spatial space resolution when the X-ray collection image is collected.

The three-dimensional image combining unit 26 according to the third embodiment combines the three-dimensional images, similarly to the first and second embodiments. For example, as illustrated in FIG. 12, the three-dimensional image combining unit 26 combines the first three-dimensional image with the second three-dimensional image. The three-dimensional image combining unit 26 according to the third embodiment preferentially uses the second three-dimensional image in an overlap area between the first three-dimensional image and the second three-dimensional image.

In this embodiment, the Feldkamp method is given as an example of the reconstruction method, but the embodiment is not limited thereto. For example, an iterative reconstruction method, such as an algebraic reconstruction technique (ART), may be used. In this embodiment, it is premised that various kinds of correction are not performed in the reconstruction process, but the embodiment is not limited thereto. For example, correction, such as scattered ray correction, beam hardening correction, and ring correction, may be performed.

In this embodiment, the second reconstruction area is at the center of the first reconstruction area. However, the embodiment is not limited thereto, and the second reconstruction area may deviate from the center. However, since a phenomenon, such as the deterioration of image quality, is likely to occur in the periphery of the first reconstruction area, it is not preferable that the second reconstruction area greatly deviate from the center.

Figure 17:
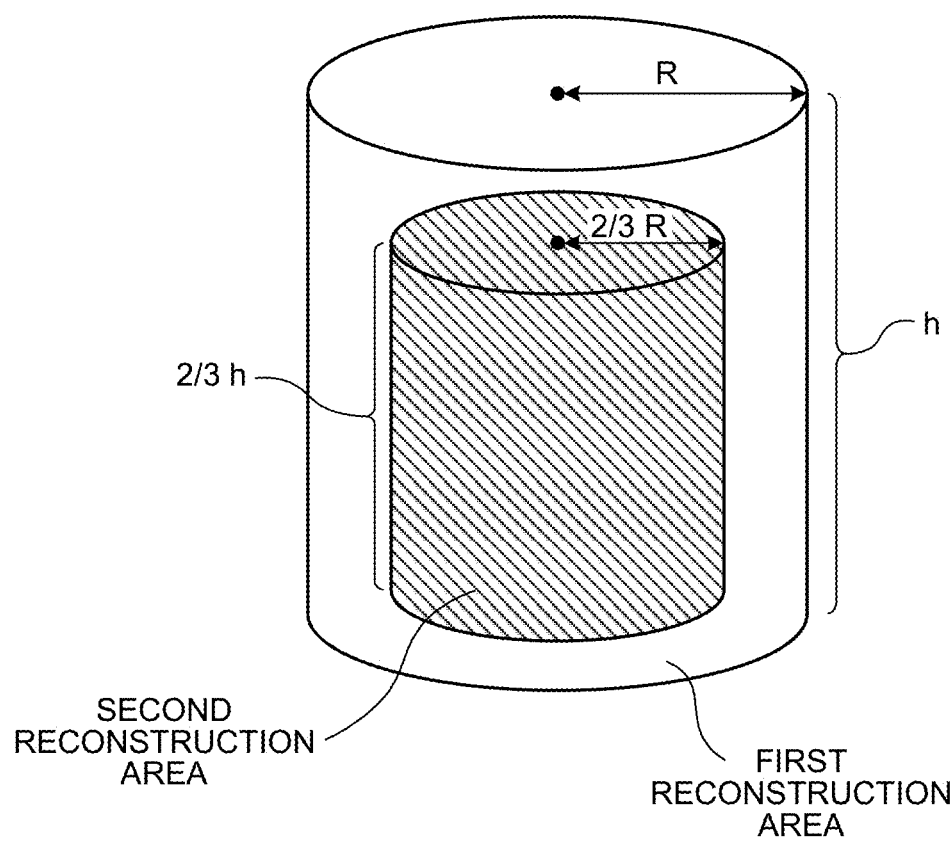
FIG. 17 is a diagram illustrating the position of a second reconstruction area according to the third embodiment.

FIG. 17 is a diagram illustrating the position of the second reconstruction area according to the third embodiment. For example, as illustrated in FIG. 17, it is preferable that the second reconstruction area be in an area included in a cylinder with a radius that is two-thirds of the radius "R" of the first reconstruction area and a height that is two-thirds of the height "h" of the first reconstruction area.

Figure 18:
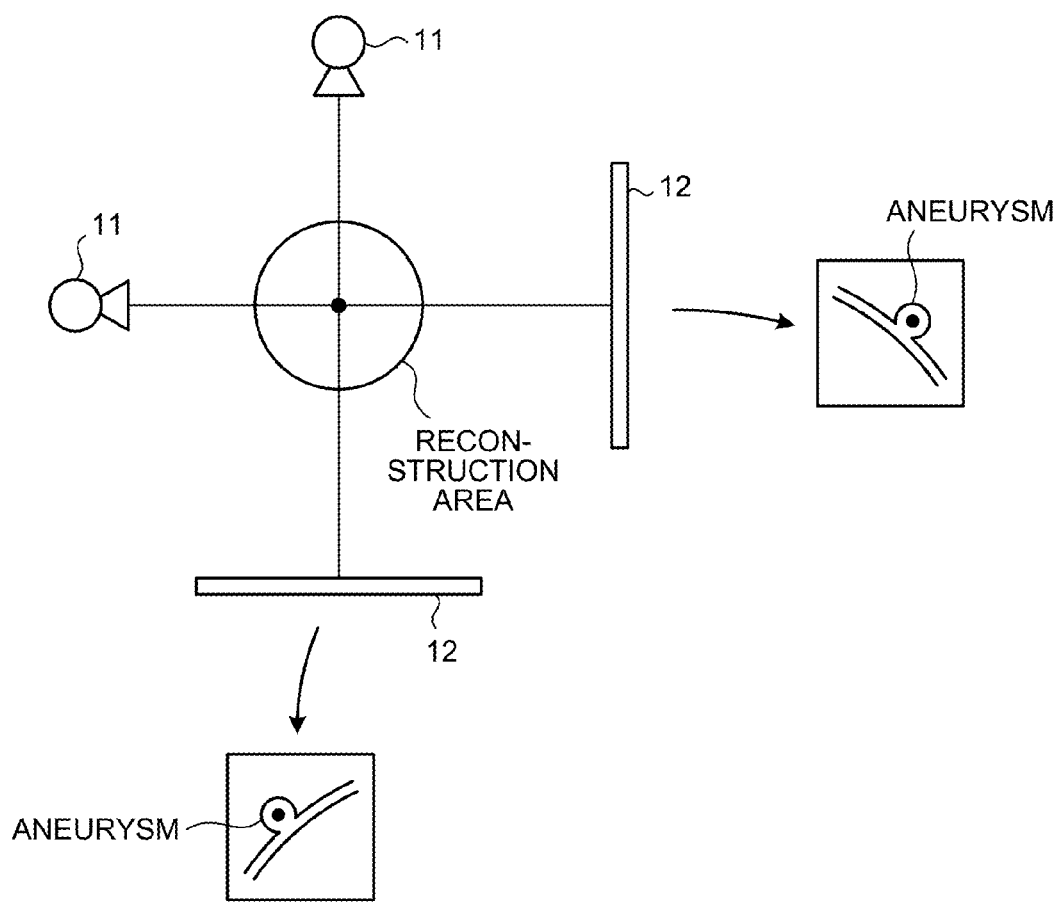
FIG. 18 is a diagram illustrating the designation of the position of the second reconstruction area according to the third embodiment.
Figure 19:
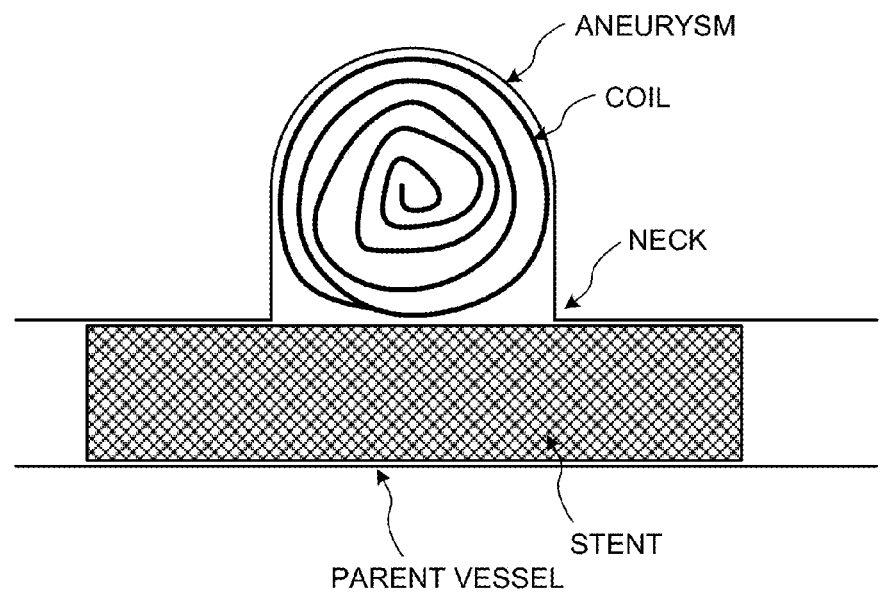
FIG. 19 is a diagram illustrating a coiling treatment using a stent.
Figure 20:
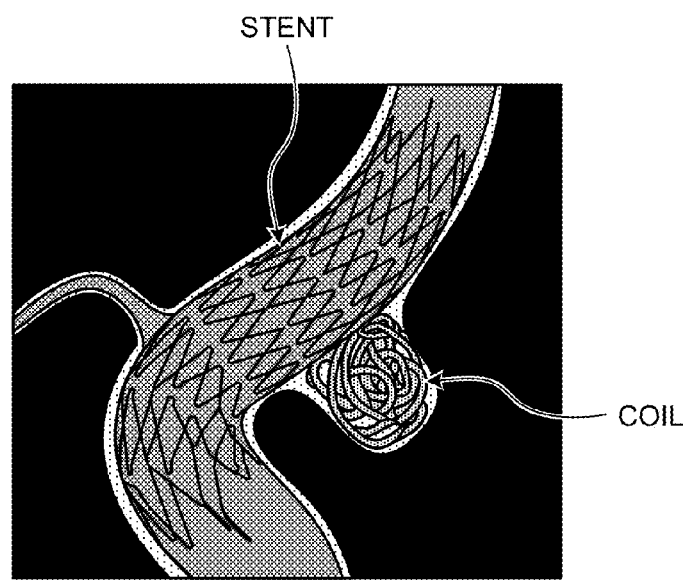
FIG. 20 is a diagram illustrating the coiling treatment using the stent.

In addition, for example, there is a method of designating the position of the second reconstruction area on the X-ray collection image which is collected at an angle of about 90 degrees. FIG. 18 is a diagram illustrating the designation of the position of the second reconstruction area according to the first embodiment. In FIG. 18, a central circle indicates the cylinder of the first reconstruction area or the second reconstruction area, as viewed from the upper side. As illustrated in FIG. 18, for example, when the position of the aneurysm on the X-ray collection image at two angles (for example, at an angular interval of about 90 degrees) relative to the cylinder is designated, the position of the aneurysm in a three-dimensional space is determined. The three-dimensional reconstruction unit 24 may extract the X-ray projection image in the second reconstruction stage such that the aneurysm determined in the three-dimensional space is disposed at the center.

In this way, according to the third embodiment, it is possible to achieve both the extraction of a wide area (for example, the entire area in the field of view) and the extraction of a clear area of interest at the same time. For example, it is possible to satisfy clinical needs for minutely observing the area of interest including the stent while checking the overall structure of the vessels and for significantly reducing the amount of exposed dose to the patient.

The three-dimensional reconstruction unit 24 according to the third embodiment performs a convolution filtering process when the first three-dimensional image and the second three-dimensional image are generated. The high-frequency emphasis effect of the convolution filtering process performed when the second three-dimensional image is generated is more than that of the convolution filtering process performed when the first three-dimensional image is generated.

In this way, according to the third embodiment, it is possible to extract a clear image of the area of interest.

(First Modification)

In the third embodiment, the three-dimensional image combining unit 26 simply combines the first three-dimensional image with the second three-dimensional image, but the embodiment is not limited thereto. In some cases, the pixel levels (density values) of the first three-dimensional image and the second three-dimensional image are different from each other due to some factors, such as various correction effects. Therefore, it is preferable that the three-dimensional image combining unit 26 compare the pixel level of a portion of the first three-dimensional image corresponding to the second reconstruction area with the pixel level of the second three-dimensional image and perform the correction. For example, the three-dimensional image combining unit 26 calculates the difference (AV1−AV2) between the average pixel level AV2 of the second three-dimensional image and the average pixel level AV1 of a portion of the first three-dimensional image corresponding to the second reconstruction area and adds the difference (AV1−AV2) to the pixels of the second three-dimensional image. This is global correction.

The three-dimensional image combining unit 26 may perform local correction after the global correction. For example, the three-dimensional image combining unit 26 compares the average pixel level of a small area (for example, a size of 32 pixels×32 pixels) of the second three-dimensional image with the average pixel level of a small area of the first three-dimensional image corresponding to the small area of the second three-dimensional image and performs correction such that there is no large difference between the two pixel levels. When the correction is performed in this way, the pixel levels of the first three-dimensional image and the second three-dimensional image are adjusted and the boundary between the two images is smoothly extracted from the combined three-dimensional image. In addition, the correction described in the first modification may be similarly applied to the first and second embodiments.

(Second Modification)

In the third embodiment, the three-dimensional reconstruction unit 24 (first reconstruction unit 24a) performs the reducing process as the pre-process of the first-stage reconstruction. However, the three-dimensional reconstruction unit 24 may perform a low-pass filtering process, not the reducing process, on the X-ray collection image and may reconstruct the filtered image subjected to the low-pass filtering process. For example, when the low-pass filter is of a type in which a value is reduced to one-fourth in an area with a size of 2 pixels×2 pixels, the same effect as that when the reducing process is performed is obtained.

In addition, the three-dimensional reconstruction unit (first reconstruction unit 24a) may combine a given low-pass filter with a convolution filter as the first-stage reconstruction and may directly perform a reconstruction process on the X-ray collection image using the combined filter. In this modification, the discrete interval of the first-stage reconstruction is not necessarily the length "2d". For example, the three-dimensional reconstruction unit 24 (first reconstruction unit 24a) may perform reconstruction at a discrete interval of a length "1.5d" using a low-pass filter which is slightly sharper than the low-pass filter equivalent to the reducing process.

(Third Modification)

In the third embodiment, the three-dimensional reconstruction unit 24 (second reconstruction unit 24b) extracts only a central portion with a size of 512 pixels×1,024 pixels and performs reconstruction. However, the second-stage reconstruction attaches importance to spatial resolution rather than to density resolution. Therefore, the three-dimensional reconstruction unit 24 (second reconstruction unit 24b) may extract a central portion with a size of 512 pixels×512 pixels, instead of extracting the portion with a size of 512 pixels×1,024 pixels and process the extracted portion. In this case, the density resolution of the reconstructed image is reduced a little, but the filtering process ends in a short time.

In this case, the second three-dimensional image generated by the three-dimensional reconstruction unit 24 (second reconstruction unit 24b) is reconstructed from the X-ray projection image with a size of 512 pixels×512 pixels, not the X-ray projection image with a size of 512 pixels×1,024 pixels. Therefore, the three-dimensional reconstruction unit 24 (second reconstruction unit 24b) can generate the data of only the inside of the cylinder illustrated in FIG. 15 and cannot generate the data of the outside of the cylinder, which is also the data of the inside of a cube with a size of 512×512×512 voxels (a predetermined value is appropriately given).

(Fourth Embodiment)

As the medical image processing device according to the embodiment, the X-ray diagnosis apparatuses according to some embodiments have been described above, but the embodiment is not limited thereto.

[Modality]

For example, the medical image processing device according to each of the embodiments may be incorporated into an X-ray CT apparatus. In addition, for example, the medical image processing device according to each of the embodiments may be a single medical image processing device. In this case, the medical image processing device acquires the X-ray collection image collected by the medical image diagnosis apparatus and generates a three-dimensional image on the basis of the acquired X-ray collection image. For example, the medical image processing device may be connected to the medical image diagnosis apparatus, such as an X-ray diagnosis apparatus or an X-ray CT apparatus, through a network and receive the X-ray collection image from the medical image diagnosis apparatus, thereby acquiring the X-ray collection image.

When a single medical image processing device is used, the medical image processing device includes the three-dimensional reconstruction unit 24 and the three-dimensional image combining unit 26 according to the above-described embodiments. The A/D conversion unit 21 and the subtraction unit 23 may be appropriately provided according to the format of data, for example, whether data received from the medical image diagnosis apparatus is an analog signal, an X-ray collection image converted into a digital signal, or an X-ray projection image subjected to the subtraction process. The two-dimensional image storage unit 22 and the three-dimensional image storage unit 25 may be appropriately provided according to an operation form, for example, whether the storage device is provided inside or outside the medical image processing device. The monitor 28 may be appropriately provided according to an operation form, for example, whether the display device is provided inside or outside the medical image processing device.

[Convolution Filter]

In the third embodiment, the "first-stage reconstruction" is performed on the basis of the data subjected to the pre-process and the "second-stage reconstruction" is performed on the basis of the data which has not been subjected to the pre-process. Since the pre-process is similar to a process equivalent to the process to which the "smooth" convolution filter is applied, the convolution filter applied to each of the "first-stage reconstruction" and the "second-stage reconstruction" is not necessarily changed. For example, the same convolution filter may be used.

[Area of Interest Other than Stent]

In the above-described embodiments, an example of extracting the clear image of the stent in the intervention treatment is given, but the case in which the medical image processing device is applied is not limited thereto. When the user wants to extract a wide area and the clear image of the area of interest at the same time, the medical image processing device may be similarly applied. For example, the medical image processing device may be similarly applied when the user wants to extract the clear image of a part with a complicated structure, such as the bone of the ear, as the area of interest.

[Numerical Example]

Various numerical values (for example, "1,024" and "512") are illustrative, and may be arbitrarily changed depending on, for example, an operation form.

According to the medical image processing device according to at least one of the above-described embodiments, it is possible to clearly observe both the stent and the vessels.

Some embodiments of the invention have been described above. However, these embodiments are illustrative, but are not intended to limit the scope of the invention. These embodiments can be performed in other various ways, and various omissions, substitutions, and changes can be made without departing from the scope and spirit of the invention. These embodiments or modifications thereof are included in the scope and spirit of the invention and are also included in the scope of equivalents to the invention disclosed in the claims.

What is claimed is:

1. A medical image processing device comprising:
  subtraction circuitry configured to generate a DSA (Digital Subtraction Angiography) image between a first X-ray collection image collected before a contrast medium is injected and a second X-ray collection image collected after the contrast medium is injected;

first reconstruction circuitry configured to generate a first reconstructed image in which a vessel is depicted on the basis of the DSA image using a first reconstruction filter;

second reconstruction circuitry configured to generate a second reconstructed image in which a stent placed into the vessel is depicted on the basis of the first X-ray collection image collected before the contrast medium is injected by using a second reconstruction filter having a high-frequency emphasis effect more than that of the first reconstruction filter and by adjusting at least one of a window width and a window level; and image combining circuitry configured to combine the first reconstructed image in which the vessel is depicted with the second reconstructed image in which the stent is depicted.

2. The medical image processing device according to claim 1, further comprising:

specifying circuitry; and identification circuitry, wherein, the stent includes stent markers provided at both ends thereof, the specifying circuitry applies the first reconstruction filter to the image before the contrast medium is injected to generate a third reconstructed image, and performs threshold processing on the third reconstructed image to specify the stent markers, the identification circuitry identifies an area of interest surrounded by the stent markers in the third reconstructed image, and the second reconstruction circuitry applies the second reconstruction filter to the area of interest in the image before the contrast medium is injected and generates the second reconstructed image for the area of interest.

3. The medical image processing device according to claim 1, further comprising:

specifying circuitry; and identification circuitry, wherein, the stent includes stent markers provided at both ends thereof, the specifying circuitry applies the first reconstruction filter to the image before the contrast medium is injected to generate a third reconstructed image, and performs threshold processing on the third reconstructed image to specify the stent markers, the identification circuitry identifies an area of interest surrounded by the stent markers in the second reconstructed image, and the image combining circuitry combines the first reconstructed image with the area of interest identified in the second reconstructed image.

4. The medical image processing device according to claim 1, wherein the first reconstruction circuitry performs a reducing process or a low-pass filtering process as a pre-process on the X-ray collection image and applies a reconstruction filter to the X-ray collection image subjected to the reducing process or the low-pass filtering process, thereby generating the first reconstructed image.

5. The medical image processing device according to claim 4, wherein the length of one side of a voxel forming the first reconstructed image is equal to, or more than, 1.5 times the length of one size of a voxel forming the second reconstructed image.

6. The medical image processing device according to claim 1, wherein the image combining circuitry further corrects the densities of the first reconstructed image and the second reconstructed image.

7. The medical image processing device according to claim 6, wherein the image combining circuitry performs correction using the average of pixel values in a part of the second reconstructed image and the average of pixel values in a part of the first reconstructed image corresponding to the part of the second reconstructed image.

8. A medical image processing device comprising:

first reconstruction circuitry configured to generate a first reconstructed image in which a vessel is depicted on the basis of an X-ray collection image capturing the image of the vessel and an image of a stent placed into the vessel using a first reconstruction filter;

specifying circuitry;

identification circuitry, second reconstruction circuitry configured to generate a second reconstructed image in which the stent placed into the vessel is depicted on the basis of the X-ray collection image by using a second reconstruction filter having a high-frequency emphasis effect more than that of the first reconstruction filter and by adjusting at least one of a window width and a window level; and image combining circuitry;

wherein the stent includes stent markers provided at both ends thereof, the specifying circuitry performs threshold processing on the first reconstructed image to specify the stent markers, the identification circuitry identifies an area of interest surrounded by the stent markers in the first reconstructed image, the second reconstruction circuitry applies the second reconstruction filter to the area of interest in the X-ray collection image and generates the second reconstructed image for the area of interest in which the stent is depicted, and the image combining circuitry combines the first reconstructed image in which the vessel is depicted with the second reconstructed image for the area of interest in which the stent is depicted.

9. A medical image processing device comprising:

first reconstruction circuitry configured to generate a first reconstructed image in which a vessel is depicted on the basis of an X-ray collection image capturing the image of the vessel and an image of a stent placed into the vessel using a first reconstruction filter;

second reconstruction circuitry configured to generate a second reconstructed image in which the stent placed into the vessel is depicted on the basis of the X-ray collection image by using a second reconstruction filter having a high-frequency emphasis effect more than that of the first reconstruction filter and by adjusting at least one of a window width and a window level;

specifying circuitry;
identification circuitry, and
image combining circuitry;
wherein
the stent includes stent markers provided at both ends thereof,
the specifying circuitry performs threshold processing on the first reconstructed image to specify the stent markers,
the identification circuitry identifies an area of interest surrounded by the stent markers in the second reconstructed image, and
the image combining circuitry combines the first reconstructed image in which the vessel is depicted with the area of interest identified in the second reconstructed image in which the stent is depicted.

* * * * *